(12) United States Patent
Qi et al.

(10) Patent No.: US 11,567,053 B2
(45) Date of Patent: Jan. 31, 2023

(54) OIL DISPERSANT EFFECTIVENESS MONITORING

(71) Applicant: COMMONWEALTH SCIENTIFIC AND INDUSTRIAL RESEARCH ORGANISATION, Australian Capital Territory (AU)

(72) Inventors: Xiubin Qi, Acton (AU); Emma Crooke, Acton (AU); Andrew Ross, Acton (AU); Christine Trefry, Acton (AU); Mederic Mainson, Acton (AU)

(73) Assignee: COMMONWEALTH SCIENTIFIC AND INDUSTRIAL RESEARCH ORGANISATION, Australian Capital Territory (AU)

( * ) Notice: Subject to any disclaimer, the term of this patent is extended or adjusted under 35 U.S.C. 154(b) by 627 days.

(21) Appl. No.: 16/498,678

(22) PCT Filed: Mar. 29, 2018

(86) PCT No.: PCT/AU2018/050302
§ 371 (c)(1),
(2) Date: Sep. 27, 2019

(87) PCT Pub. No.: WO2018/176106
PCT Pub. Date: Oct. 4, 2018

(65) Prior Publication Data
US 2020/0041477 A1 Feb. 6, 2020

(30) Foreign Application Priority Data
Mar. 31, 2017 (AU) .............................. 2017901184

(51) Int. Cl.
*G01N 33/18* (2006.01)
*G01N 33/28* (2006.01)
(Continued)

(52) U.S. Cl.
CPC ..... *G01N 33/1833* (2013.01); *G01N 15/0205* (2013.01); *G01N 15/14* (2013.01);
(Continued)

(58) Field of Classification Search
None
See application file for complete search history.

(56) References Cited

U.S. PATENT DOCUMENTS

| 4,434,364 A | 2/1984 | Correa et al. |
| 5,929,453 A * | 7/1999 | Andrews ............ G01N 33/1833 250/461.1 |

(Continued)

FOREIGN PATENT DOCUMENTS

| GB | 2273355 | * 6/1994 |
| WO | 2013/104954 | 1/2012 |

OTHER PUBLICATIONS

International Search Report for PCT/AU2018/050302, dated Jun. 6, 2018, 5 pages.
(Continued)

*Primary Examiner* — Daniel S Larkin
(74) *Attorney, Agent, or Firm* — Nixon & Vanderhye PC

(57) ABSTRACT

A process is provided for the determination of oil dispersant effectiveness. A submersible dispersant sensing platform is passed across a body of water. The platform has a plurality of sensors including a multichannel fluorometer and a particle size analyser, and each sensor produces an output data stream. The body of water is continuously analysed at a predetermined depth profile below the surface of the body of water. Hydrodynamic and environmental condition data is collected proximate in time and location to the output data from the dispersant sensing platform. The environmental condition data includes one or more of ambient temperature, body or water temperature, salinity of the body of water, (Continued)

wind speed, location, mixing energy of the body of water and derivatives thereof. Oil and dispersant data is provided which includes characteristics of the dispersant and of oil samples prior to the application of the dispersant. The output data stream, the hydrodynamic and environmental condition data, and the oil and dispersant data is processed to generate an indicator of the state of dispersion of the oil and of the oil dispersant efficiency under the hydrodynamic and environmental conditions the oil is exposed to. A system for the determination of oil dispersant efficacy is also provided.

21 Claims, 10 Drawing Sheets

(51) Int. Cl.
  G01N 15/02  (2006.01)
  G01N 15/14  (2006.01)
  G01N 21/64  (2006.01)
  G01N 15/00  (2006.01)
(52) U.S. Cl.
  CPC .............. G01N 21/64 (2013.01); G01N 33/28 (2013.01); *G01N 2015/003* (2013.01); *G01N 2015/1402* (2013.01); *G01N 2015/1493* (2013.01)

(56) References Cited

U.S. PATENT DOCUMENTS

| | | | |
|---|---|---|---|
| 7,198,755 B2 | 4/2007 | Tokhtuev et al. | |
| 9,834,460 B2* | 12/2017 | Nedwed | ............. G01N 33/1826 |
| 2017/0232435 A1* | 8/2017 | Sieben | ................. G01N 21/645 |
| | | | 436/2 |

OTHER PUBLICATIONS

Written Opinion of the ISA for PCT/AU2018/050302, dated Jun. 6, 2018, 7 pages.
Examination Report dated Feb. 4, 2022 in Australian Application No. 2018241255, 3 pages.
Fitzpatick, M., et al., "Detection of Oil in Water Column: Sensor Design", Acquisition Directorate Research & Development Center, Feb. 2013, Report No. CG-D-05-13, pages I to C-4 (50 pages in total).
WET Labs Inc.—WETStar Fluorometer User's Guide, Oct. 2010 [retrieved from internet on May 24, 2017] 29 pages. http://www.bodc.ac.uk/data/documents/nodb/pdf/wetlabs_wetstar.pdf.
Li, Z. et al., "Assessment of Chemical Dispersant Effectiveness in a Wave Tank under Regular Non-Breaking and Breaking Wave Conditions", Marine Pollution Bulletin, 2008, vol. 56, pp. 903-912.
Balsley, A. et al., "Detection of Oil within the Water Column", 2014 International Oil Spill Conference Proceedings, May 2014, 299483, pp. 2206-2217. https://doi.org/10.7901/2169-3358-2014.1.2206.

* cited by examiner

OIL DISPERSANT EFFECTIVENESS MONITORING

This application is the U.S. national phase of International Application No. PCT/AU2018/050302 filed 29 Mar. 2018, which designated the U.S. and claims priority to Australian Provisional Patent Application No. 2017901184 filed on 31 Mar. 2017, the contents of which are to be taken as incorporated herein by this reference.

TECHNICAL FIELD

The invention relates to a system and a method for sub surface testing of oil spill dispersant effectiveness, in particular, in the context of marine oil spill dispersants for surface slicks.

BACKGROUND OF INVENTION

When oil is spilled at sea, a small proportion will be naturally dispersed by the mixing action caused by waves. This process can be slow and proceed to only a limited extent for most situations. Dispersants are used to accelerate the removal of oil from the surface of the sea by greatly enhancing the rate of natural dispersion of oil and thus prevent it from coming ashore. Dispersed oil will also be more rapidly biodegraded by naturally occurring microorganisms. The rationale for dispersant use is that dispersed oil is likely to have less overall environmental impact than oil that persists on the surface of the sea, drifts and eventually contaminates the shoreline, where it can damage coastal habitats and resident wildlife.

Thus, any discharge of a significant amount of oil into the marine environment may trigger a response effort to recover or dissipate the spilled oil. Although mechanical recovery of the oil is the primary means of removing large quantities of spilled oil, application of chemical dispersants is an important supplementary measure for spills that spread over a wide area or create a large slick.

The effectiveness of a particular dispersant is difficult to assess, partly because it depends on a variety of factors. Clearly, the composition of the dispersant product and the application system are important factors in determining the effectiveness of the dispersant. Other important factors are the composition and state of the oil being dispersed, the ratio of dispersant to oil, temperature, water salinity and the amount of mixing energy in the environment. Oil composition can vary considerably through the weathering process, from light crude oils which will evaporate to a significant degree, to medium crude oils with different amounts of aromatics, saturates, resins and asphaltenic and polar compounds, to heavy crude oils and fuel products with lower volatility and higher viscosity. In addition, the oil can become emulsified with water, causing a significant increase in volume and viscosity. Both weathering and emulsification can make oil dispersion more difficult.

There are several lab based dispersant effectiveness methods developed by different parties, including the SFT (Swirling Flask Method) and the Mackay method. Though taking different forms, the principles of these methods are quite similar. They all involve loading a fixed amount of sample oil on the surface of water pre-filled in a container, treating the oil with a specific ratio of oil dispersant to be assessed and introducing consistent mixing energy to facilitate oil dispersion and then allow the mixture to settle for a consistent amount of time before quantification of oil dispersed in the water phase of the oil remain on the surface. However, since dispersant efficacy is affected by a wide range of factors, therefore although results from laboratory assessment of dispersant efficacy provide critical information for pre-screening of dispersant to be used in the field, these results will not represent the actual performance of the dispersants in the natural environment, and hence the need to monitor the dispersant effectiveness directly in the field to provide information guiding oil spill response operations.

Currently the only standard way of conducting field in situ dispersant efficacy is the SMART (Special Monitoring of Applied Response Technologies) system developed by NOAA. It is only composed of one channel of a fluorometer and relies on its enhanced response to give an indication of oil dispersion. The system is also vulnerable to interference from turbulence caused by ship movement.

WO2013104954 addressed this issue through disclosing a system for testing the oil spill dispersing effectiveness of a dispersant through simulating the effect of a dispersant in a stirred vessel and measuring at least one parameter relevant to the dispersant's effectiveness. Whilst this method is convenient it is a lab based, small scale setup and suffered from the inherent limitation of stimulating the effects of the ocean in a small vessel.

A reference herein to a patent document or any other matter identified as prior art, is not to be taken as an admission that the document or other matter was known or that the information it contains was part of the common general knowledge as at the priority date of any of the claims.

SUMMARY OF INVENTION

In one aspect of the present invention, there is provided a process for the determination of oil dispersant effectiveness, the process including the steps of:
  A. passing a submersible dispersant sensing platform across a body of water; said platform having a plurality of sensors including a multichannel fluorometer and a particle size analyzer, each sensor producing an output data stream;
  B. continuously analyzing the body of water at a predetermined depth profile below the surface of the body of water;
  C. collecting hydrodynamic and environmental condition data proximate in time and location to the output data from the dispersant sensing platform, said environmental condition data including one or more of: ambient temperature; body or water temperature; salinity of the body of water; wind speed; location; mixing energy of the body of water and derivatives thereof;
  D. providing oil and dispersant data including characteristics of the dispersant and of oil samples prior to the application of the dispersant; and
  E. processing the output data stream, the hydrodynamic and environmental condition data, and the oil and dispersant data to generate an indicator of the state of dispersion of the oil and of the oil dispersant efficiency under the hydrodynamic and environmental conditions the oil is exposed to.

The body of water is preferably an open body of water, such as an ocean or lake, although the system may also be advantageously applied to confined bodies of water, such as a wave tank or a flume tank.

The use of a multichannel fluorometer in combination with a particle size analyzer to characterise the oil dispersion in the determination of oil dispersant efficacy has found particularly beneficial when combined with hydrodynamic and environmental data in providing an accurate and robust result, which may be used to inform decision making as to the management of oil spills through applying dispersants.

In some embodiments, the processing step E further includes analyzing the oil dispersion efficiency through multi-variate analysis. The multi-variate analysis may include discriminant analysis, such as linear discriminant analysis, and preferably, principal component analysis. The processing step E preferably further includes analyzing the state of dispersion of the oil through pattern analysis. Pattern analysis of the sensor output data and derivatives thereof may enable the fingerprint of the oil spill to be more readily identified. Preferably, the analysis involves multi-variate analysis, which may involve linear discriminant analysis and principal component analysis. Other forms of discriminant analysis may also be used. The analysis may also involve multiple discriminant analysis to allow compression of the multi-variate signal to support the classification process.

Multi-variate analysis of obtained multi-sensor response, coupled with a regression model, identifies significant factors controlling the in situ sensor response spectra. Given the possibility that a set of sensor response pattern can be associated with a particular level of dispersion efficiency (DE), it may consequently be possible to build a library to archive the average in situ sensor response patterns based on measurements conducted in a wave tank with controllable, quantifiable dispersion energy and quantitative DE. Subsequently, given field sensor response data, it is possible to predict oil dispersions states and DE under specific field conditions of field hydrodynamic and environmental conditions and oil and dispersant characteristics. With enough field data, the correlation between DE and oil characteristics and dispersant characteristics and field conditions can be created. Ultimately, given field hydrodynamic and environmental conditions, oil and dispersant characteristics, it is possible to use the correlation to predict oil dispersion efficiency in the field without the need to conduct actual water monitoring.

The ability to correlate and model multiple variants enables the many signals affecting the sensor outputs to be taken into account, with this "noise" thereby able to be filtered out to produce a standardised fingerprint which may be more readily compared to other standardised fingerprints.

In a preferred embodiment, the analysis uses a database including one or more of:
  (i) characteristics of oil samples prior to the application of the dispersant;
  (ii) sensor output when monitoring oil samples at various stages of dispersion within a field environment;
  (iii) sensor output when monitoring oil samples at various stages of dispersion within a controlled environment;
  (iv) hydrodynamic and environmental condition data in respect to (ii) and/or (iii);
  (v) characteristics of the dispersant; and
  (vi) correlations or models based upon (iii) and dispersion efficiency (DE) under one or more of (i), (iv) and (v).

In some embodiments, the correlations or models are based upon (iii) and DE under all of (i), (iv) and (v).

The use of comparable reference data of oil dispersant efficacy, environment and hydrodynamic condition data may enable correlations or models with enhanced accuracy and utility to be developed and deployed.

The correlations or models are preferably used to predict the oil dispersion characteristics over time, under a specific set of hydrodynamic and environmental conditions, and optionally, oil type/state and type of dispersant. More preferably, at least a portion of the database includes oil dispersant efficacy data and obtained sensor output when monitoring oil samples at various stages of dispersion within a controlled environment. The controlled environment may be a testing tank with controlled hydrodynamic and environmental conditions or an open field environment with controlled oil release.

In some embodiments, the processing step E further includes quantitatively estimating or determining the oil dispersant efficiency. The correlations or models may be used to quantitatively determine or estimate the oil dispersant efficiency based on at least sensor output (ii). The correlations or models may be used to quantitatively determine or estimate the oil dispersant efficiency based on a ratio between the first two principal components of principal component analysis of sensor output (ii). Preferably, the ratio is principal component 2/principal component 1 (PC2/PC1). The sensor output (ii) may include sensor output from the multichannel fluorometer, and optionally, from all three fluorometer channels. Accordingly, oil dispersant efficiency may be determined or estimated based on sensor output from three fluorometer channels, and subsequently processed using principal component analysis to provide correlations or models to provide a quantitative estimate of dispersion efficiency.

Field evaluation of chemical dispersion efficiency is of great challenge due to the complexity of open water characteristics in the field. Conversely, direct measurement of multiple sensor response fingerprint data may improve field quantification of oil dispersion efficiency.

To ensure that the oil spill sensor (e.g. fluorometer, particle size analyzer and optionally turbidity meter) data is sufficiently time synchronised with the environment and hydrodynamic condition data. The hydrodynamic and environmental condition data is preferably collected within a two-hour window from when the dispersed oil sample is analysed by the sensing platform. More preferably, the hydrodynamic and environmental condition data is collected within a ten-minute window from when the dispersed oil sample is analysed by the sensing platform. To enhance the accuracy of the correlation, the hydrodynamic and environmental conditional data is preferably collected on a frequent basis.

Preferably, the environmental condition data may be sourced directly from sensors mounted on the sensing platform and weather stations onboard the deployment vessel or in close proximity thereto. The advantage of have environment sensors in close proximity to the sensing platform is that environmental condition data will be more specific to the actual conditions experienced by the samples being continuously analysed. Alternatively, the hydrodynamic and environmental condition data may be collected within a 10 km window, and more preferably within a 1 km window, from when the dispersed oil sample is analysed by the sensing platform. In some embodiments, the environment data may be sourced from local environmental monitoring stations which supply accessible information via the internet.

Periodic or more preferably continuous acquisition of environment condition data, either through automated or manual analysis and future analysis of oil state may be tagged to the oil dispersant efficacy data, with the combination of the two used to produce a correlation as to the progression of oil dispersant which may preferably be used to predict the future oil dispersant progression.

The analysis preferably results in a recommendation to initiate actions in regard to the type, quantity and/or timing of the application of more dispersant to the body of water.

The analysis results may be compared against one or more reference standards in regard to the expected oil dispersant efficacy and, depending upon such a comparison, a decision making algorithm may make recommendations for specific actions to be initiated to enhance effectiveness of the oil dispersant use. The recommended actions preferably include a confidence limit attached thereto.

Preferably, the submersible dispersant sensing system further includes a depth sensor to monitor the distance of the sensors from the surface of the body of water.

As the state of dispersion of the oil is typically dependent upon the depth below the surface that it is analysed, it is important that deviations from the desirable sample analysis depth are identified. The variance in the analysis depth of the water may be taken into account during the processing and/or analysis of the output data stream, thereby enabling enhanced data quality resulting in a more accurate indicator of the status of the state of dispersion of the oil.

The submersible dispersant sensing system preferably further includes a temperature sensor to monitor water temperature, thereby enabling the sensor data to be corrected for temperature dependencies.

In some embodiments, the process further includes the steps of:
recording hydrodynamic and environmental condition data and the sensor output data (D0) during transit in control area with no oil slick for baseline correction;
recording hydrodynamic and environmental condition data and the sensor output data (D1) during transit in area below oil slick prior to dispersant A application; and
recording hydrodynamic and environmental condition data and the sensor output data (D2) during transit in area below oil slick post to dispersant A application,
wherein the processing step D is used to identify relative spatial difference between the naturally dispersed oil and chemically dispersed oil to decide if the two groups of sensor output data D1 and D2 are statistically different.

In some embodiments, the process further includes the steps of:
recording hydrodynamic and environmental condition data and the sensor output data (D0) during transit in control area with no oil slick for baseline correction;
recording hydrodynamic and environmental condition data and the sensor output data (D1) during transit in area below oil slick prior to dispersant application;
recording hydrodynamic and environmental condition data and the sensor output data (DA) during transit in area below oil slick post to dispersant A application;
recording hydrodynamic and environmental condition data and the sensor output data (DB) during transit in area below oil slick post to dispersant B application; and
recording hydrodynamic and environmental condition data and the sensor output data (DC) during transit in area below oil slick post to dispersant C application,
wherein the processing step D is used to determine if the corresponding groups of sensor output data DA, DB and DC are statistically different and, if so, quantify the spatial distance between groups.

In some embodiments, the process further includes the steps of:
recording hydrodynamic and environmental condition data and the sensor output data (D0) during transit in control area with no oil slick for baseline correction;
recording hydrodynamic and environmental condition data and the sensor output data (D1) during transit in area below oil slick prior to dispersant A application;
recording hydrodynamic and environmental condition data and the sensor output data (DOR1) during transit in area below oil slick post to dispersant A application at predetermined DOR (Dispersant vs Oil ratio);
recording hydrodynamic and environmental condition data and the sensor output data (DOR2) during transit in area below oil slick post to dispersant A application with increased DOR; and
recording hydrodynamic and environmental condition data and the sensor output data (DOR3) during transit in area below oil slick post to dispersant A application with further enhanced DOR,
wherein the processing step D is used to determine if the corresponding groups of sensor output data DOR1, DOR2 and DOR3 are statistically different.

In another aspect of the present invention, there is provided a system for the determination of oil dispersant efficacy, the system including:
a submersible dispersant sensing platform including a multichannel fluorometer and a particle size analyzer each producing an output data stream;
a means to pass the submersible dispersant sensing platform through a body of water;
a source of oil and dispersant data including characteristics of the dispersant and of oil samples prior to the application of the dispersant; a source of hydrodynamic and environmental condition data;
a processing unit for receiving the output data stream, the hydrodynamic and environmental data, and the oil and dispersant data, and for generating an indicator of the state of dispersion of the oil and of the oil dispersant efficiency under the hydrodynamic and environmental conditions the oil is exposed to; and
a communication means for communicating the output data stream, the hydrodynamic and environmental condition data, and the oil and dispersant data to the processing unit.

The means to pass the submersible dispersant sensing platform through a body of water may include means to tow the platform, such as by use of a cable attached to the platform and optionally, a monitoring vessel. Accordingly, the platform may be towed by means of a cable attached between the monitoring vessel and the platform to pass the platform through a body of water. Alternatively, the platform may itself be self-propelled. For example, the platform may include a propeller, which may be included in a tail fin of the platform, for passing the platform through a body of water.

The communications means may include a communications device for communicating the data. The communications device may be wired or wireless and may include a network device. The data may be communicated between the platform and the processing unit.

In some embodiments, the processing unit further includes a report generating module.

The processing unit preferably includes a sub-module for pre-processing the output data stream and pre-processing the hydrodynamic and the environment condition data. For example, the pre-processing may be used to monitor and/or correct for variations in sensor depth and/or water temperature. The pre-processing may also be used for baseline corrections from a body of water including no oil slick and/or dispersant.

Preferably, the submersible dispersant sensing platform further includes a turbidity sensor producing an output data stream to correct for interference from a field water matrix effect. The use of a turbidity meter in combination with a particle size analyzer may enable a more accurate and robust assessment of the oil particle degradation state.

In some embodiments, the system further includes an analysis unit for analyzing the oil dispersant efficiency through multi-variate analysis. The system preferably further includes an analysis unit for analyzing the state of dispersion of the oil through pattern analysis. In a preferred embodiment, the system further includes a database including one or more of:
(i) characteristics of oil samples prior to the application of the dispersant;
(ii) sensor output when monitoring oil samples at various stages of dispersion within a field environment;
(iii) sensor output when monitoring oil samples at various stages of dispersion within a controlled environment;
(iv) hydrodynamic and environmental condition data in respect to (ii) and/or (iii);
(v) characteristics of the dispersant; and
(vi) correlations or models based upon (ii) and dispersion efficiency (DE) under one or more of (i), (iv) and (v).

In some embodiments, the correlations or models are based upon (iii) and DE under all of (i), (iv) and (v).

In some embodiments, the processing unit is further adapted to quantitatively estimate or determine the oil dispersant efficiency. In some embodiments, the correlations or models are used to quantitatively determine or estimate the oil dispersant efficiency based on at least sensor output (ii). The correlations or models may be used to quantitatively determine or estimate the oil dispersant efficiency based on a ratio between the first two principal components of principal component analysis of sensor output (ii). Preferably, the ratio is principal component 2/principal component 1 (PC2/PC1). The sensor output (ii) may include sensor output from the multichannel fluorometer, and preferably from three fluorometer channels. Accordingly, oil dispersant efficiency may be determined or estimated based on sensor output from three fluorometer channels, and subsequently processed using principal component analysis to provide correlations or models to provide a quantitative estimate of dispersion efficacy.

Preferably, the multichannel fluorometer is configured to measure the emission fluorescence of the aqueous solution over the wavebands of at least a portion of each wavelength band 300 nm to 380 nm, 360 nm to 520 nm, and 410 nm to 600 nm using a corresponding excitation band length of at least a portion of each wavelength band between 214 nm and 294 nm, 214 nm and 294 nm, and 205 nm and 445 nm, respectively. It has been found that this specific combination of wavelength ranges provides key fingerprint data relating to the state of oil dispersion.

In some embodiments, the multichannel fluorometer includes a separate light source for each channel. In other embodiments, the multichannel fluorometer includes a shared light source for each channel. Preferably, the light source is a LED or xenon light source. In other embodiments, the fluorometer includes a common xenon lamp light that has three individual excitation filters. The portion of each wavelength band is preferably at least 50% of each wavelength band and more preferably at least 90% of each wavelength band.

In a preferred embodiment, the body of water is within a testing tank under controlled environmental conditions or within a field environment. The use of a testing tank enables process parameters to be more accurately controlled and thereby enables more robust models to be developed. In contrast to laboratory testing, the size of the testing tank is also sufficiently large to enable the models to correlate well with field conditions.

In another aspect of the present invention, there is provided a computer readable medium, in which a computer program is stored which, when executed by a processor, is adapted to control or carry out one or more steps of the inventive process as described herein.

BRIEF DESCRIPTION OF DRAWINGS

The invention will now be described in greater detail with reference to the accompanying drawings in which like features are represented by like numerals. It is to be understood that the embodiments shown are examples only and are not to be taken as limiting the scope of the invention as defined in the claims appended hereto.

DETAILED DESCRIPTION

Embodiments of the invention are discussed herein by reference to the drawings which are not to scale and are intended merely to assist with explanation of the invention. This specification uses the terms dispersant efficiency and dispersant efficacy for DE interchangeably, as would be appreciated by a person skilled in the art.

Figure 1:
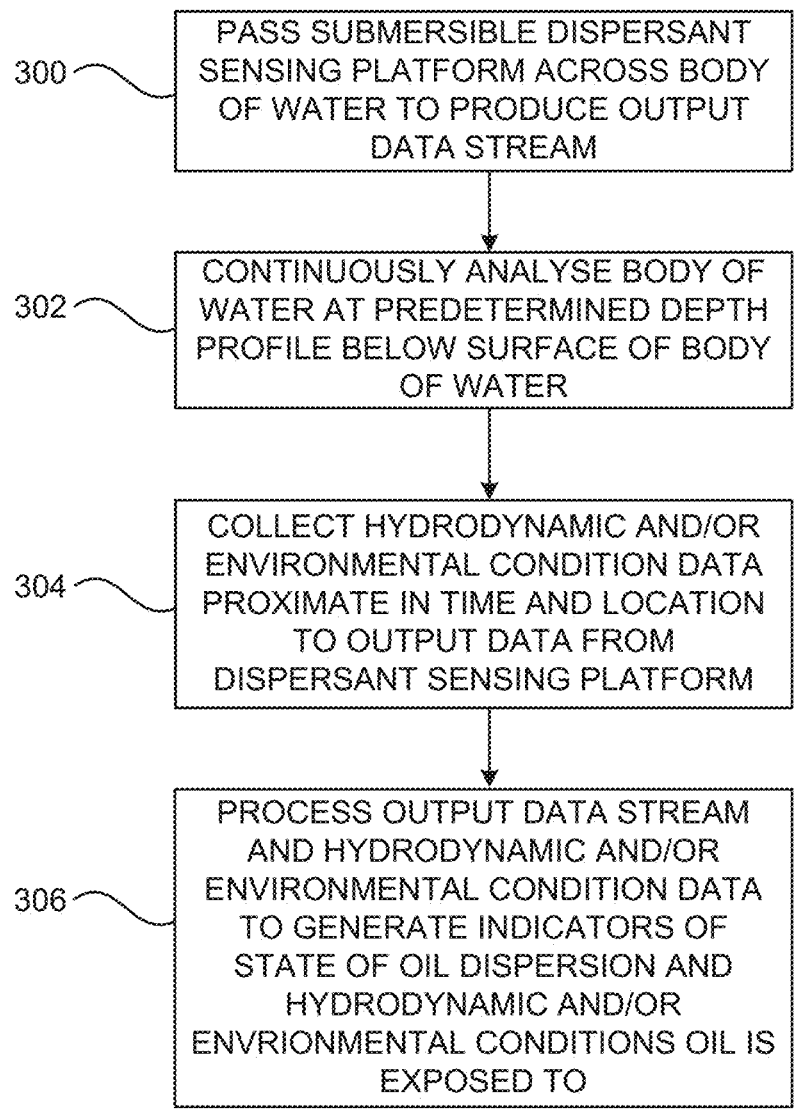
FIG. 1 is a flow chart of a process for the determination of oil dispersant efficacy according to an embodiment of the present invention.

In a preferred embodiment of the present invention, there is provided a process for the determination of oil dispersant efficacy, as illustrated in FIG. 1. The process includes the step 300 of passing a submersible dispersant sensing platform 100 across a body of water. The platform 100 has a plurality of sensors including a multichannel fluorometer 20 and a particle size analyzer 30, and each sensor produces an output data stream (see also FIGS. 6 and 7). The process also includes the step 302 of continuously analyzing the body of water at a predetermined depth profile below the surface of the body of water. The process further includes the step 304 of collecting hydrodynamic and environmental condition data proximate in time and location to the output data from the dispersant sensing platform 100. The environmental condition data includes one or more of: ambient temperature; body or water temperature; salinity of the body of water; wind speed; location; mixing energy of the body of water and/or derivatives thereof. The process further includes the step 306 of providing oil and dispersant data including characteristics of the dispersant and of oil samples prior to the application of the dispersant. The process further includes the step 308 of processing the output data stream, the hydrodynamic and environmental condition data, and the oil and dispersant data to generate an indicator of the state of dispersion of the oil and of the oil dispersant efficiency under the hydrodynamic and environmental conditions the oil is exposed to.

Figure 2:
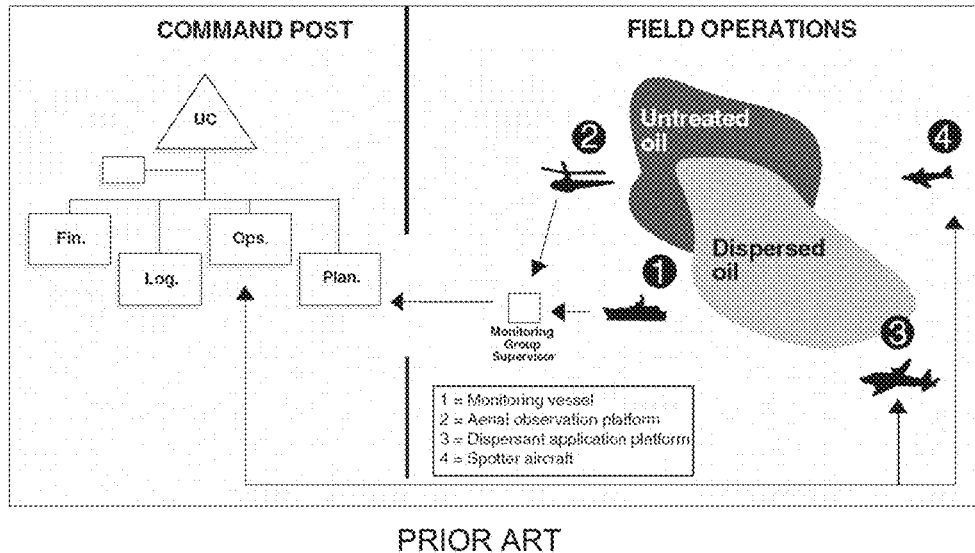
FIG. 2 is a schematic diagram illustrating the command, control and data flow relating to managing an oil spill through the use of an oil dispersant.
Figure 3:
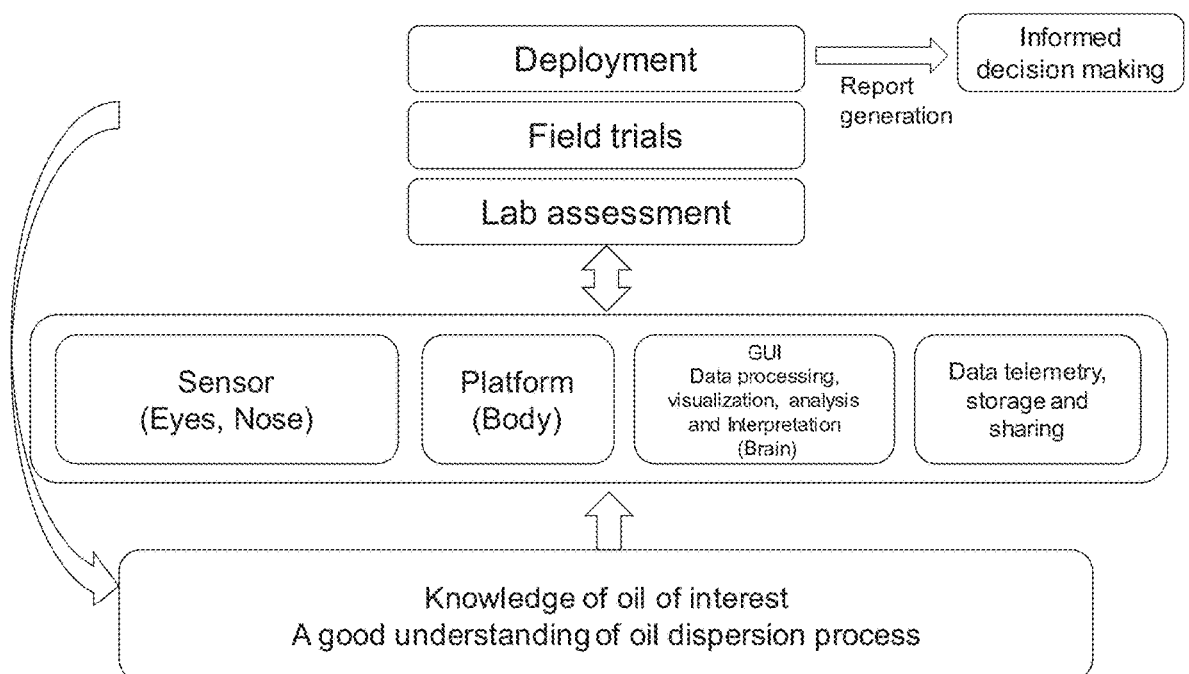
FIG. 3 is a schematic diagram illustrating the process of converting knowledge relating to oil dispersion into a form which may be used for informed decision making.

The management of oil spills, as illustrated in FIG. 2, is often a major logistical operation in which unified command (UC) needs to know whether operations (Ops) is initiating action to efficiently and effectively disperse the oil. The operation may include a monitoring vessel 1 for providing real time assessment of the state and extent of oil dispersal. The monitoring vessel 1 is preferably supported by an aerial observation platform 2 and spotter aircraft 4 to visually provide data to the extent of an oil spill and to enable the transect survey to be designed.

Preferably, the dispersant application platform 3 (e.g. aerial dispersant delivery) delivers an amount and type of dispersant dependent upon the information provided from the monitoring vessel 1 and to a location indicated by the aerial observation platform 2. The field data is preferably analysed with planning (Plan.) determining the course of action dependent upon the risk assessment and given financial constraints (Fin.).

There are three common operational activities, with survey tracks being designed and planned accordingly.

Assessment of Effectiveness of One Dispersant Application

In one embodiment, the process further includes the steps of:
recording hydrodynamic and environmental condition data and sensor output data (D0) during transit in control area with no oil slick for baseline correction;
recording hydrodynamic and environmental condition data and sensor output data (D1) during transit in area below oil slick prior to dispersant A application; and
recording hydrodynamic and environmental condition data and sensor output data (D2) during transit in area below oil slick post to dispersant A application.

The data processing step 308 is used to identify relative spatial difference between the naturally dispersed oil and chemically dispersed oil to decide if the two groups of sensor output data D1 and D2 are statistically different.

Compare and Rank Multiple (2 or More) Dispersant Effectiveness

In another embodiment, the process further includes the steps of:
recording hydrodynamic and environmental condition data and sensor output data (D0) during transit in control area with no oil slick for baseline correction;
recording hydrodynamic and environmental condition data and sensor output data (D1) during transit in area below oil slick prior to dispersant application;
recording hydrodynamic and environmental condition data and sensor output data (DA) during transit in area below oil slick post to dispersant A application;
recording hydrodynamic and environmental condition data and sensor output data (DB) during transit in area below oil slick post to dispersant B application; and
recording hydrodynamic and environmental condition data and sensor output data (DC) during transit in area below oil slick post to dispersant C application.

The data processing step 308 is used to determine if the corresponding groups of sensor output data DA, DB and DC are statistically different and, if so, quantify the spatial distance between groups.

Determination of Optimum Dispersant Application Ratio

In a further embodiment, the process further includes the steps of:
recording hydrodynamic and environmental condition data and sensor output data (D0) during transit in control area with no oil slick for baseline correction;
recording hydrodynamic and environmental condition data and sensor output data (D1) during transit in area below oil slick prior to dispersant A application;
recording hydrodynamic and environmental condition data and sensor output data (DOR1) during transit in area below oil slick post to dispersant A application at predetermined DOR (Dispersant vs Oil ratio);
recording hydrodynamic and environmental condition data and sensor output data (DOR2) during transit in area below oil slick post to dispersant A application with increased DOR; and
recording hydrodynamic and environmental condition data and sensor output data (DOR3) during transit in area below oil slick post to dispersant A application with further enhanced DOR.

The data processing step 308 is used to determine if the corresponding groups of sensor output data DOR1, DOR2 and DOR3 are statistically different.

The effectiveness and efficiency of these operations is highly dependent upon accurate real time data being available and processed and presented in a form in which an informed decision may be made. As indicated in FIG. 2, the ability to provide the required information from the deployment of a platform 100 mounted with sensors as defined in the present invention is enhanced through prior knowledge gained through field trials and laboratory assessments.

The submersible dispersant sensing platform 100 includes a suite of sensors for dispersed oil and preferably environment monitoring. The sensors may include, but are not limited to a multichannel fluorometer 20; a particle size analyzer 30; a turbidly meter; a salinity sensor; a water depth sensor; an ambient and/or water temperature sensor.

The sensing platform 100 maybe deployed either directly off the side of the operating vessel or through a fixed pulley attached to an A frame for easy retrieval.

The configuration of the platform 100 allows the system to balance and stabilize away the vessel. The length of the tow cable should ensure that the sensing platform 100 is well outside the turbulence caused by vessel bow wave or propeller.

The sensing platform 100 is preferably towed by a monitoring vessel 1, although it would be appreciated that the sensing platform 100 could also be self-propelled, the propeller should cause minimum disturbance to the waterbody to be monitored. The sensing platform 100 preferably able to operate to collect output data from the sensors at a predetermined depth profile. The depth profile may span multiple depths or be configured to maintain a constant depth. In some embodiments, the predetermined depth profile is a constant depth below the surface of the body of water. In other embodiments, the predetermined depth profile is at a variable depth below the surface of the body of water.

The monitoring equipment or sensing platform 100 is designed for the assessment of effectiveness of dispersant applied to oil spills with wide spatial coverage, i.e. preferably at least 100 $m^2$, more preferably at least 500 $m^2$, even more preferably at least 1 $km^2$ and even more preferably at least 10 $km^2$.

Figure 4:
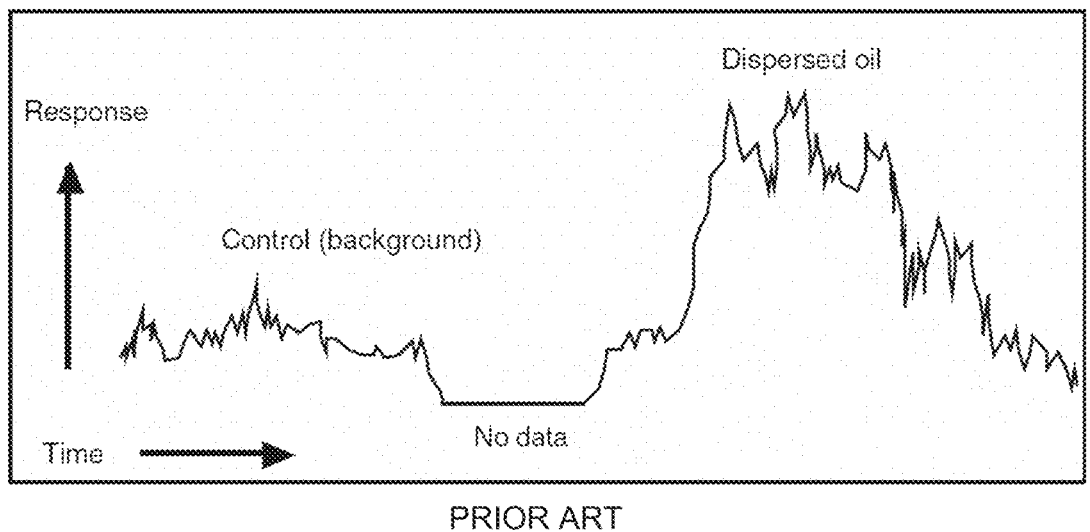
FIG. 4 is a display of a data output stream corresponding to background/control readings; no signal and readings from a dispersed oil sample.

Preferably, the sensing platform 100 passes through a body of water, which has not been subject to treatment by the dispersant, to obtain a baseline reading of the sensors, including the multichannel fluorometer 20, as illustrated in FIG. 4.

Figure 5:
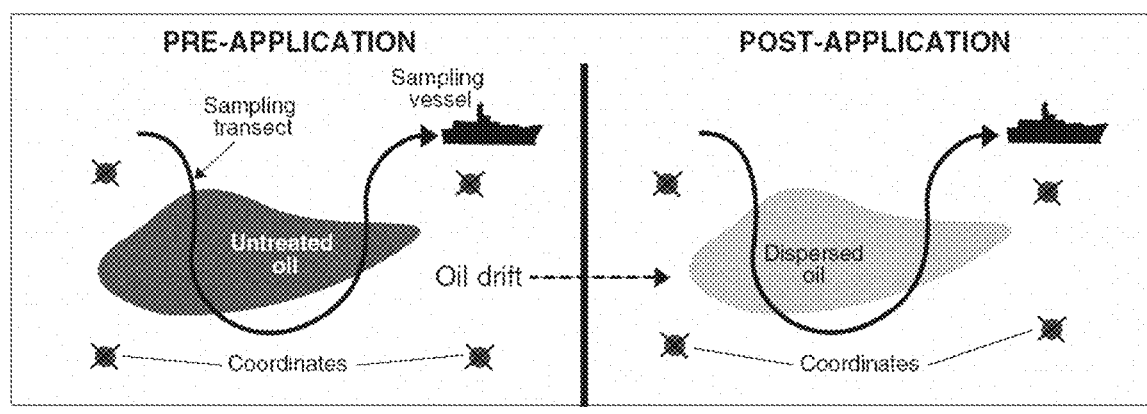
FIG. 5 is a schematic diagram indicating the transect pathways of the sensing platform.

The monitoring vessels 1 may also sample the oil spill to determine its chemical characteristics and profile to assist in determining the most appropriate dispersant to be applied. The determined oil spill characteristics may be referenced against a database of oil types and their dispersive characteristics under specific environmental conditions and dispersant type and quantity. Through having improved prior knowledge of how the oil spill will react to treatment, a more effective and efficient dispersant application plan can be implemented. As indicated in FIG. 5, the transversal of the oil spill is performed with reference to the oil spill's spatial position, with wind and wave conditions preferred used to predict the future direction and shape of the body of dispersed oil.

The design of the sensing platform 100 is preferably such that the desired depth profile maybe maintained. As indicated in the platform sensor designs of FIGS. 6 and 7, the platform 100 comprises a multichannel fluorometer 20 and a particle size analyzer 30 mounted onto a planar mounting plate 40, preferably made from a corrosive resistant material, such as powder coated aluminum. The platform 100 also preferably includes a temperature sensor and a depth sensor (not shown). The dimensions of the platform 100 shown in FIGS. 6 and 7 are indicated in millimetres (mm), however it would be appreciated by a person skilled in the art that the dimensions may be altered or varied without departing from the aspects of the invention as described herein. The constant depth sensing platform 100 in FIG. 6 comprises a buoyancy device, such as a plurality of flotation spheres 50, which are made from expanded polystyrene. The sensing platform 100 also preferably comprises a hydrofoil 25 to stabilise the flotation spheres 50 of the sensing platform 100 on the top of the body of water, when in use. The planar mounting plate 40 is preferably mounted on a float plate 45, which includes the flotation spheres 50 and hydrofoil 25 as shown in FIG. 6B.

Figure 6A:
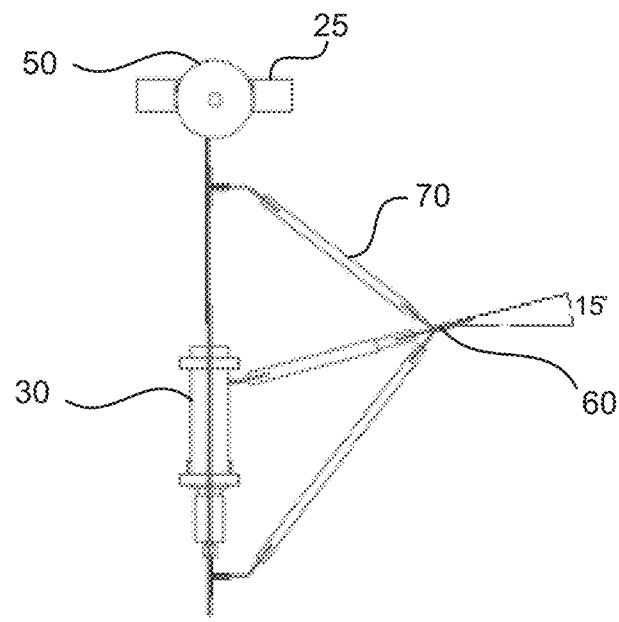
FIGS. 6A and 6B illustrate a sensing platform configured to collect data at a constant depth under the surface of the body of water according to an embodiment of the present invention, showing a side view (FIG. 6A) and plan view (FIG. 6B).

In a preferred embodiment, the distance of the sensors below the flotation spheres 50 maybe adjusted, preferably between 0.5 to 3 metres and more preferably between 1 to 2 meters below a central horizontal axis of the flotation spheres 50. The maintenance of the sensors away from the operating vessel (such as monitoring vessel 1) is assisted through regulating the cable length 60 mounted to a three-arm pivoted towing frame 70 and maintaining a steady monitoring vessel speed, which is preferably below 8 knots and more preferably below 5 knots. The angle of the towing frame is preferably set for a vertical angle of the tow cable to be about 15 degrees when in use as illustrated in FIG. 6A. It is desirable to maintain a vertical position of the mounting plate 40, to avoid vertical force components acting upon the mounting plate 40 thereby deviating from the desired depth profile.

Figure 6B:
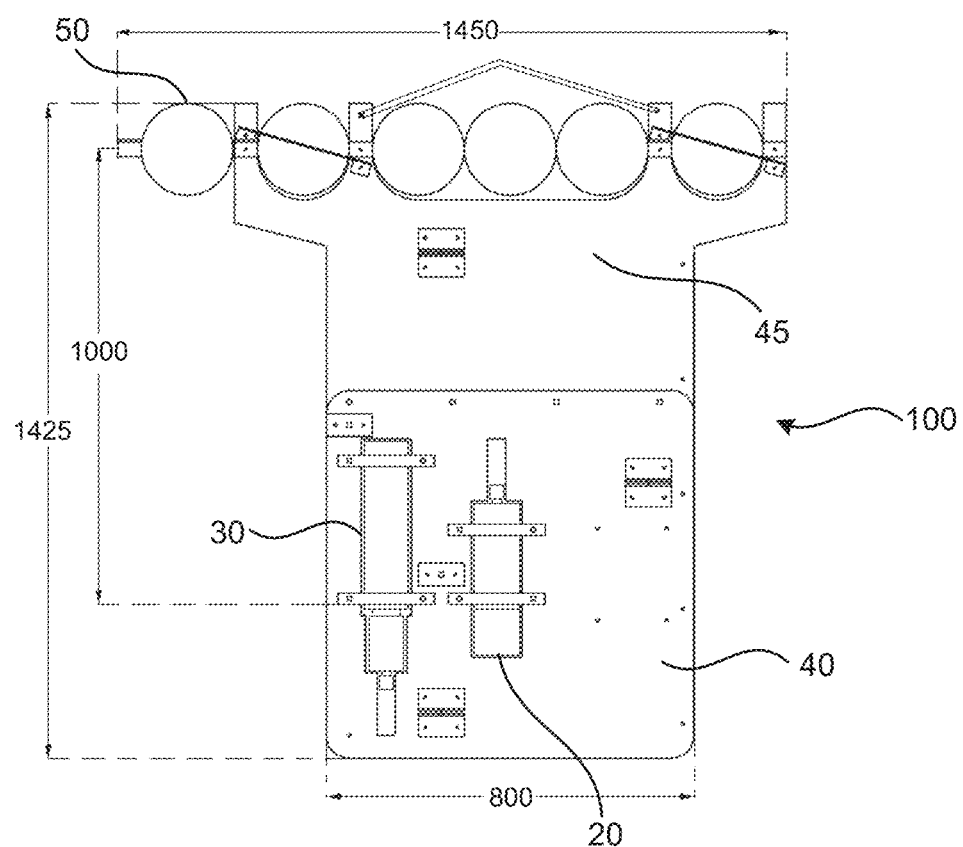
Figure 7A:
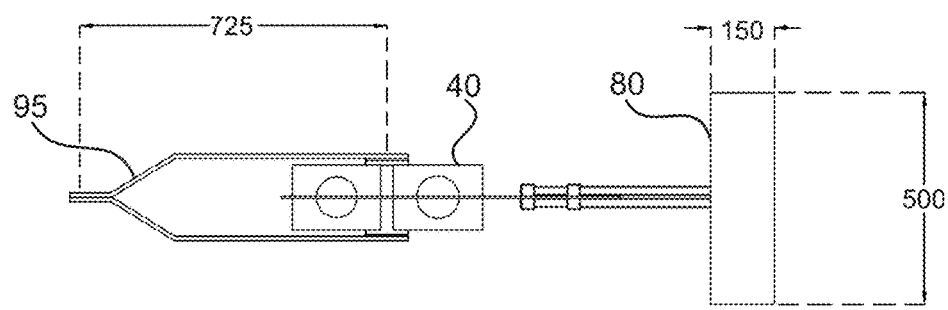
FIGS. 7A, 7B, and 7C illustrate a sensing platform configured to collect data at variable depths under the surface of the body of water according to an embodiment of the present invention, showing a side view (FIG. 7A), plan view (FIG. 7B), and rear view (FIG. 7C).
Figure 7B:
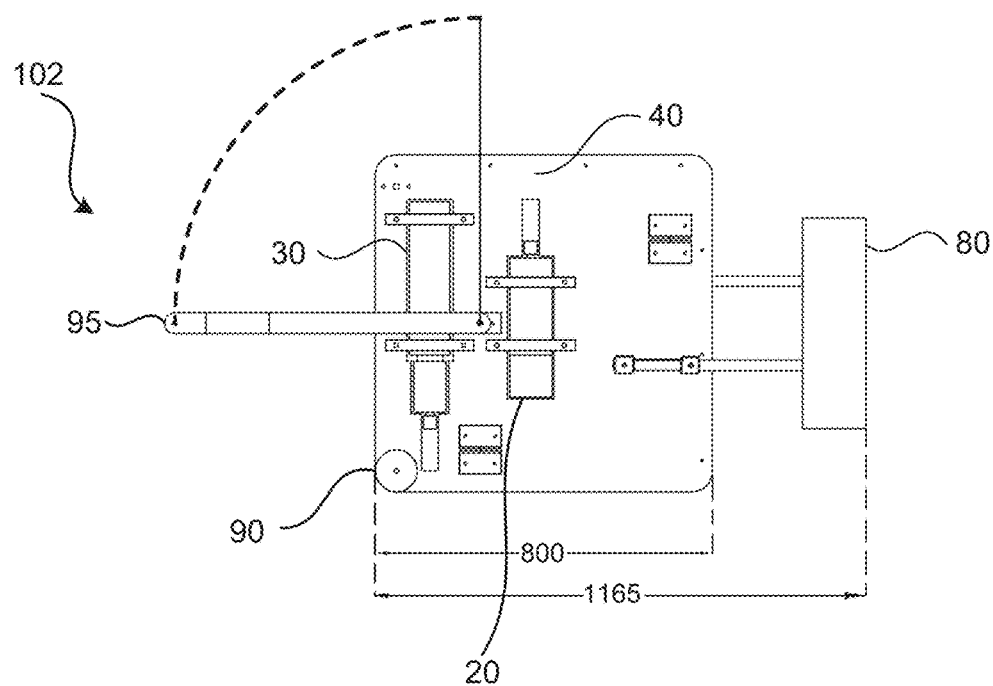
Figure 7C:
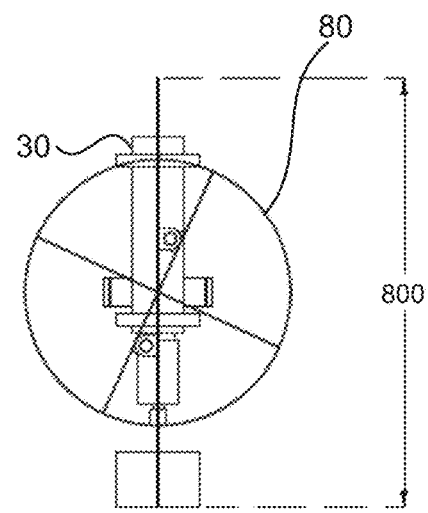

The multiple depth sensing platform 102 in FIGS. 7A to 7C preferably shares the same sensors 20, 30 and mounting plate 40 as the constant depth sensing platform 100 of FIGS. 6A and 6B, but with the flotation spheres 50 and hydrofoil 25 removed and replaced with a tail fin 80 to stabilise the substantially vertical plane as the sensing platform 102 preferably passes through the body of water, as shown in FIGS. 7A and 7C. As shown in FIG. 7B, the mounting plate 40 also preferably includes demountable weights 90 to enable the sensing platform 102 to be appropriately weighed for the depth profile and the speed of the sensing platform 102 passing through the body of water. In addition to the adjustable weight, the depth profile may be controlled through varying the speed of the sensing platform 102 as well as the length of cable released from the monitoring vessel 1, which is connected to a pivoted mounting arm 95.

Processing and Analysis

Oil spills produce a fluorescence fingerprint characteristic of the oil composition and its physical characteristics, including particle size. Although the sensor output from the multichannel fluorometer 20 and the particle size analyzer 30 is theoretically sufficient in itself to determine the state of oil dispersion, the complexities of environmental factors affecting this output is such that it is preferably that the output data stream is processed in combination with accompanying environmental data in a pre-processing step prior to the processed data being analysed.

Prior to use, the sensors are preferably inspected, calibrated and tested for damage, data communication and sensing performance (baseline drift and sensitivity) prior to commissioning. All sensor data collected is preferably subject to QA/QC to ensure sufficient data quality. The QA/QC steps include eliminating bad data points resulting from sensor malfunction, noise removal and baseline correction. Sensor data from all channels are preferably collated into a table with Time/GPS Coordinates/Depth/Temperature/Sensor outputs from fluorometers/Sensor outputs from particle analyzers/Depth/Outputs from other sensors (e.g. turbidity meter). The sensor data, together with all associated deployment information are to be stored in a database 130 (see FIG. 8).

Preferably, the environmental factors include the depth of the analysis and preferably the temperature of the sample being analysed by the fluorometer 20 and particle size analyzer 30. It has been found that the pre-processing of the output data from the fluorometer 20 and particle size analyzer 30 to correct for variations in analysis depth and/or temperature is able to significantly improve the quality of the resulted corrected output data. Furthermore, through being able to correct the output data for hydrodynamic and environmental variations, the corrected output may be more accurately compared to a database 130 containing output data which has been similarly corrected.

The output of the multichannel fluorometer 20 enables an enhanced fingerprint to be extracted over wavebands of at least a portion of each wavelength band 300 nm to 380 nm, 360 nm to 520 nm, and 410 nm to 600 nm using a corresponding excitation band length of at least a portion of each wavelength band between 214 nm and 294 nm, 214 nm and 294 nm, and 205 nm and 445 nm, respectively.

However, the output data stream of the multichannel fluorometer 20 is also affected by a range of interfering parameters, such as temperature and sample depth. As such, the ability to extract reliable information from the raw data is significantly compromised without a pre-processing step. The pre-processing step preferably utilising algorithms based upon mathematical models or correlations which take into account the effect of the interfering parameters. These algorithms are preferably derived from field, pilot scale and/or laboratory testing analysis oil spills or the same or similar chemical composition and physical state.

By implementing such analysis scheme in a computer system, huge amounts of data may be evaluated which can no more be handled by a human being alone, for instance by a scientist. Hidden patterns or motifs being typical for specific oil spills, may be evaluated in a multi-dimensional data space, to find a best match in a specifically efficient manner by a computer system. This may enable significantly improve reliability of measurement results and a strongly increased efficiency which would never be achievable without the database-based evaluation and preferably the multi-variant analysis. While the use of ratios of particular fluorescence wavelength have provided some benefits in analysis, the utilization of more sophisticated analysis techniques, such as multi-variant and linear discriminant analysis greatly enhances the accuracy and robustness of the methodology.

Figure 8:
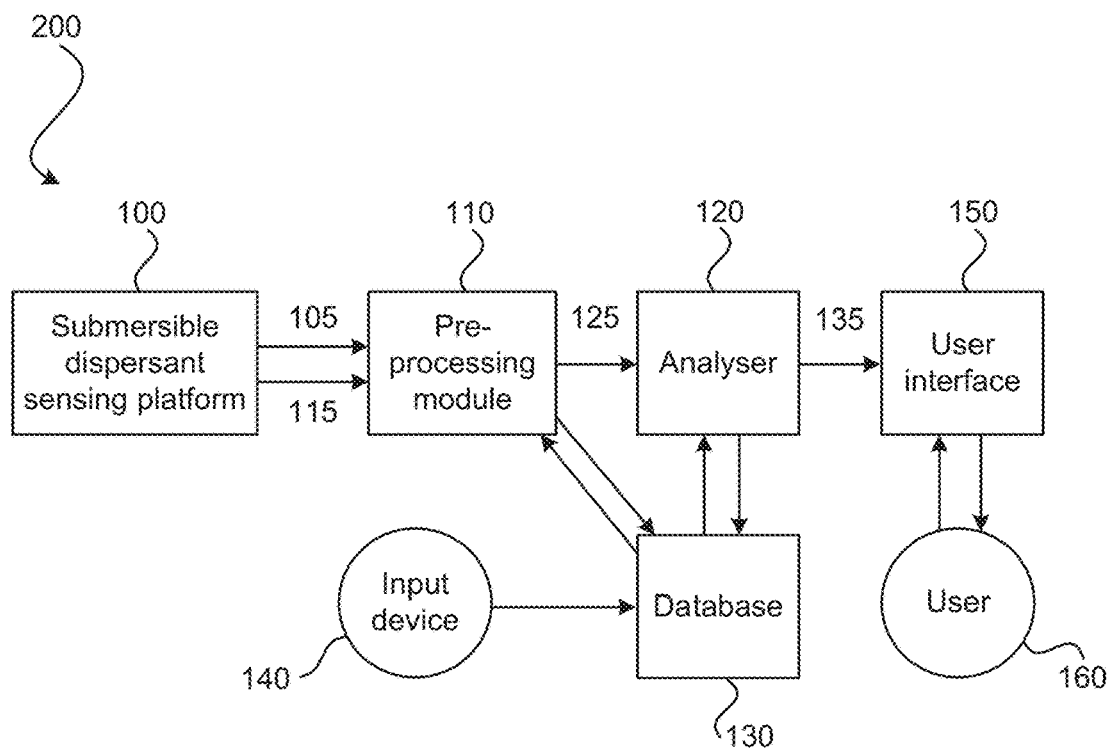
FIG. 8 is a schematic diagram of a system for the determination of oil dispersant efficacy according to an embodiment of the present invention.

In a preferred embodiment of the present invention, there is provided a system 200 for the determination of oil dispersant efficacy as illustrated in FIG. 8. The system 200 includes a submersible dispersant sensing platform 100 including a multichannel fluorometer 20 and a particle size analyzer 30 each producing an output data stream. The system 200 also includes a means to pass the submersible dispersant sensing platform 100 through a body of water. The means may include towing the platform 100 by a monitoring vessel 1, such as by means of a cable attached between the monitoring vessel 1 and the platform 100 as illustrated in FIG. 6A. Alternatively, the platform 100 may itself be self-propelled. For example, a propeller may be included in the tail fin 80 as illustrated in FIG. 7C. A person skilled in the art would appreciate various ways in which the platform 100 could be passed through a body of water.

The system 200 also includes a source of oil and dispersant data including characteristics of the dispersant and of oil samples prior to the application of the dispersant. The source of data may be from a database in communication with the system 200, or from collected oil and dispersant data. The system 200 also includes a source of hydrodynamic and environmental condition data. The source of the data may be directly from the sensors of the sensing platform 100 or from weather stations onboard the monitoring or deployment vessel 1 or in close proximity thereto. The system 200 also includes a processing unit 110 for receiving the output data stream, the hydrodynamic and environmental data, and the oil and dispersant data, and for generating an indicator of the state of dispersion of the oil and of the oil dispersant efficiency under the hydrodynamic and environmental conditions the oil is exposed to. The system 200 further includes a communications means for communicating the output data stream, the hydrodynamic and environmental condition data, and the oil and dispersant data to the processing unit 110. The communications means may include a communications device for communicating the data. The communications device may be wired or wireless and may include a network device. The data may be communicated between the platform 100 and the processing unit 110.

As illustrated in FIG. 8, the sensing platform 100 produces a multichannel fluorometer output data stream 105 indicative of an oil spill at a specific geographic location and stage of dispersal is obtained and is supplied to a pre-processing module 110. The pre-processing module 110 maybe a CPU of a computer system, a microprocessor, a separate computer, or the like. It will be capable of controlling the pre-processing module 110 for processing the output data 105. The pre-processing module 110 preferably utilises additional output data streams 115, such outputs from a depth sensor and/or a temperature sensor, to correct the output data from interfering parameters. The pre-processing module 110 may also refine and correct the output data through utilising comparative data from a database 130. The database 130 preferably contains comparative output data from previous field deployments of the sensing platform 100 as well as test results from laboratory and pilot scale simulations.

After being pre-processed the output data stream 105 is converted to a standardised output data form 125 which may be more accurately compared with other standardised output data which populates the database 130, such as EEPROM or other such memory 130.

The standardised output data 125 is then analysed to determine the corresponding oil spill's state of dispersal and corresponding dispersive efficiency. Multi-variant analysis is preferably used to extract the key features differentiating the oil dispersion states in a multidimensional space, and analyzing if the differences are mainly due to variation of characteristic features of fluorometer responses and blue shift of the oil droplets distribution.

The analysis preferably includes comparison of the standardised output data 125 with a collection of data items stored in the database 130. The database 130 which is accessible by the pre-processing module and/or a CPU/analyzer 120 (in a read and/or write mode) and which comprises a collection of data items characteristics for oil spills of different origins and/or state of dispersion. The analyzer 120 preferably preforms multidimensional analysis using pattern recognition algorithms to best match the characteristics of the oil spill sample and the characteristics of the reference oil spill standardised data stored in the database 130.

The aim of the analysis may include determining if the two groups of data (test sample and database reference) are statistically different or quantify the relative spatial difference between the naturally dispersed oil and chemically dispersed oils in a multidimensional space. A dispersive efficiency score may be determined therefrom.

The CPU 120 determines the best match(es) and outputs data 135, preferably via a report generation module (not shown), indicative of the state of oil spill dispersion from which the dispersion efficiency (DE) may be determined and displays it to a user 160, for instance via an input/output device or user interface 150.

The user interface 150 is preferably adapted for a bidirectional (data) communication with a user 160 and preferably comprises a graphical user interface (GUI) via which a user 160 may communicate with the system 200. This may include input elements like a keypad, a trackball, a joystick or even a microphone of a voice recognition system. Further, a display unit may be provided in the user interface like an LCD device, a TFT device, a plasma display or the like. Therefore, even a user 160 without specific skills may operate the analysis system 200, for instance to verify a correctness of an origin of an oil spill which has been optionally analysed within a laboratory.

The output data 135 is preferably presented by a visualisation of the data in a multidimensional format. The visualisation of the data may be accompanied by relevant performance characteristics regarding the dispersive efficiency (DE) and recommendation regarding adjustments to the dispersant concentration or location of application.

Whereas the pre-processing of the fluorometer and particle size sensor output 105 provides a transferable oil spill fingerprint 125, a predictive model of the future rate of oil spill dispersal is dependent upon predicting the environmental conditions that the oil spill will be exposed to and how the oil spill will degrade under these conditions.

Preferably, forecasts for environmental conditions such as wave energy, wind and temperature are obtained from a proximal meteorology agency. Alternatively, or in addition to, different environmental condition scenarios may be fed into an algorithm to produce a range of outcomes dependent upon the different scenarios presented. The prediction model preferably provides a probabilistic estimate of the state of oil dispersal and associated dispersal efficiency and preferably a graphical indication of the geographical distributions of the oil spill. The use of the predictive model may be used to inform the oil spill response, including the need for further application of dispersant. Preferably, the predictive response model recommends responsive actions to be taken by the user 160; and more preferably the consequence of taking such action relevant to maintaining the status quo.

The predictive model is preferably based upon data derived from the laboratory, pilot and/or field. Preferably, the predictive model is based upon data derived from a pilot facility, such as a wave tank, with a preferably minimum area of at least 10 m$^2$, preferably 50 m$^2$ and more preferably at least 100 m$^2$. Field and/or laboratory data may be manually entered into the database 130 via an input device 140, such as a computer terminal. The use of pilot plant facilities enables environmental parameters to be efficiently controlled, whilst the scale of the facilities avoids the limitations of laboratory analysis which often does not correlate well with the in field experience.

As can be taken from FIG. 8, the system 200 may be operated without the need of a human user 160 to contribute her or his skills to the system 200. Simply providing the output data 105 to the apparatus 100 will result in an output 135 indicative of the dispersive state of the source oil spill.

It is to be understood that various modifications, additions and/or alternatives may be made to the parts previously described without departing from the ambit of the present invention as defined in the claims appended hereto.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

Examples illustrating applications of embodiments of the invention will now be described. The examples are supplied to provide context and explain features and advantages of the invention and are not limiting on the scope of the invention as defined in the claims.

Example 1: Differentiation of Variable Oil Dispersion States

To obtain sensor response data used to decide dispersant effectiveness, two sensors (fluorometer 20 and particle size analyzer 30) are integrated into the dispersant effectiveness monitoring system 200. The sensors include a particle size analyzer 20 from Sequoia Technology (LISST 100X) and a three-channel fluorometer 30 (designed by CSIRO and made by Turner Designs) with the following configuration: Channel 1: 270 nm LED light source; Ex (Excitation filter): 254/40 nm; Em (Emission filter): 340/40 nm; Channel 2: 270 nm LED; Ex 254/40 nm; Em: 440/80 nm and Channel 3: 365 nm LED light; Ex 325/120 nm; Em: 410-600 nm. Various amounts of weathered Kuwait crude oil mixed with increased doses of dispersant (higher DORs) were dispersed in the salt water. Output from both sensors 20, 30 were recorded throughout the experiment. The experiment was intended to simulate dispersed oil suspended in water in the field environment, with variable DOR, oil concentration and oil dispersion energy.

To validate sensor selection and develop data interpretation protocols, the two sensors 20, 30 were evaluated in a laboratory meso scale dispersant efficacy test. The experiments were conducted in a 200 L (58 cm ID and 85 cm H) stainless steel drum with the sensors 20, 30 suspended inside. The sensors 20, 30 were tilted ~60 degrees to facilitate the flow of the oil droplets. One end of a U shaped stainless steel sampling tubing (6 mm ID) was placed next to the fluorometer 20 and the other end suspended at the outside wall of the drum. A two way valve was fitted at the end of the tubing. Oil/water suspensions were siphoned out automatically by opening the valve. The sampling tubing was only required to be primed once prior to the start of the experiment. The water inside the tubing was allowed to flow for ~20 seconds and the water samples were only collected afterwards to ensure the water samples collected represent the true composition of the water inside the drum.

Hydrodynamic and Environmental Condition Data

A mixer (Impeller type: HA715; Diameter: 120 mm), driven by a 180 watts 3 phase motor and controlled by a VSD (Variable Speed Device), was used to introduce mixing energy. The speed of the mixer can be varied by adjusting the operating frequency of the VSD controller. The mixer was mounted on a bracket fixed on a mixer stand. The height of the mixer impeller could be adjusted by moving the bracket vertically. The impeller head was set to be 45 cm from the bottom of the drum when running the experiment. A spring loaded baffle was loaded inside the drum to prevent the formation of vortex during stirring. The temperature of the oil/water suspensions was approximately 20° C.

Weathering of Crude Oil samples 30 g of the Kuwait crude oil sample was dispensed in a 200 ml jar. A magnetic stirrer was put inside the jar and the jar was placed on top of a stir plate in a fume hood. The stir bar was kept stirring to facilitate evaporation of volatile components. The oil was allowed to evaporate till 15% of the weight was lost.

Preparation of Oil/Dispersant Stock Mixture 10 g of Kuwait crude oil was dispensed into a pre labelled 100 ml glass jar, 0.2 or 0.5 g of dispersant (Ardrox 6120) was added into it to prepare stock mixtures with 1:20 or 1:50 of DOR. A magnetic stir bar was placed in the jar and kept mixing the mixture for ~20 min to create stock mixers to be used in the serial addition experiment.

Serial Addition Experiment

A total of 5 kg of NaCl (98%) was fully dissolved in ~30 L of deionized water and the salt water was then poured into the drum prefilled with 90 L of deionized water. The mixer controller's frequency was set to 10 Hz. The drum was filled up with deionized water to the 150 L marked line. The mixer was kept stirring for 20-30 min to make homogeneous salt solutions. To run a serial addition experiment, 0.5 g, 1.5 g, 1.5 g, 1.5 g of stock mixture were added in order with a syringe to the salt water under mixing. The mass of the syringe before and after mixture dispense was weighed to decide the actual mass of the stock mixture added to the drum. After each addition the solution was allowed to homogenize for 15 min before sample collection. To understand the effect of mixing energy change during oil dispersion, the speed of the mixer was varied. The detailed operating conditions were listed in Table 1 below.

TABLE 1

Mixer setting during the serial addition experiment

| Sampling point | Total stock mixture added (g) | Mixer VSD frequency (Corresponding mixing RPM) |
|---|---|---|
| 1 | 0 | 9 Hz (180 RPM) |
| 2 | 0.5 | 9 Hz (180 RPM) |
| 3 | 2 | 9 Hz (180 RPM) |
| 4 | 3.5 | 9 Hz (180 RPM) |
| 5 | 3.5 | 15 Hz (340 RPM) |
| 6 | 5 | 15 Hz (340 RPM) |
| 7 | 5 | 9 Hz (180 RPM) |
| 8 | 5 | 0 Hz (0 RPM) |

The following section describes how information from the multiple channel fluorometer 20 and the particle analyzer 30 are used to determine the more dispersed oil.

Fluorometer

Two pieces of important information can be derived from the multiple channel fluorometer 20. The first is the concentration of dispersed oil droplets which can be indicated by the signal enhancement of channel 3. The second is the characteristic property change of oil droplets at different dispersion states, which can be extracted through multivariate analysis of output from all three fluorometer channels, with the aim to differentiate states of variable states oil dispersion by visualizing clustering of specific states into distinguishable groups. The second parameter is less affected by the oil loading, in this experiment, the amount of oil added to the water drum.

An important advantage of using fluorometer over other monitoring methods is its wide dynamic range and high sensitivity. A fluorometer preferably has a low detection limit down to ppb or more preferably ppt level of dispersed oil in water. This enables a fluorometer to output higher quality valid data during field deployment compared to conventional techniques.

Particle Analyzer

Effective oil dispersion is usually accompanied by reduction of oil droplet size and greatly enhanced oil droplet concentration. The oil droplet size and concentration is preferably simultaneously captured by a particle analyzer 30. Oil droplet size is an important physical parameter characterising the status of dispersed oil, as smaller oil droplets tend to be more easily diluted and distributed by wave and current and less likely to re-coalesce and resurface. Total oil droplet concentration is preferably derived from particle size distribution histogram which can be used to confirm change of amount to dispersed oil suspended into water column. Unlike a fluorometer, the oil droplet concentration derived from a particle analyzer is in μL/L and does not require calibration to convert the sensor response to oil concentration. The particle analyzer 30 is preferably incorporated into the system 200 to validate the output of the fluorometer 20. A conflict between the expected correlation between the particle analyzer 30 and the fluorometer 20 may result in an error message and/or recommendation to calibrate the fluorometer 20.

The use of two sensors (fluorometer 20 and particle analyzer 30) avoids limitations if only relying on a particle analyzer 30 to conclude on dispersant effectiveness. Particle analyzers 30 tend to have higher detection limit (ppm level) than fluorometers 20 and may not be able to capture the above information when oil concentration is low. On the other hand, high oil concentration can also lead to faulty output from a particle analyzer 30 due to insufficient light transmission.

In addition, increasing DOR may only lead to increased amount of oil dispersed while causing minor change in oil droplet size. Therefore oil droplet size alone may not be a consistent parameter deciding dispersant effectiveness and optimum dosing rate.

Consequently information captured by a particle analyzer 30 should be combined and interpreted in conjunction with fluorometer output to generate an objective image of oil dispersion state. Fluorometer data can be used to validate particle size analyzer output when oil concentration is outside a particle analyzer's dynamic range and conversely, particle analyzer data can be used to confirm results from a fluorometer and provide additional information on oil droplet size distribution.

Results and Discussion

Channel 3 of the fluorometer has been confirmed to show good correlation between its response and the concentration of dispersed oil. Since the increase of the amount of oil below an oil slick is an indication of improved oil dispersion, the previously developed SMART kit relies on enhanced response of a fluorometer channel targeting crude oil (Channel 3 in this case) to decide oil dispersant effectiveness (Lunel, 1995).

Figure 9:
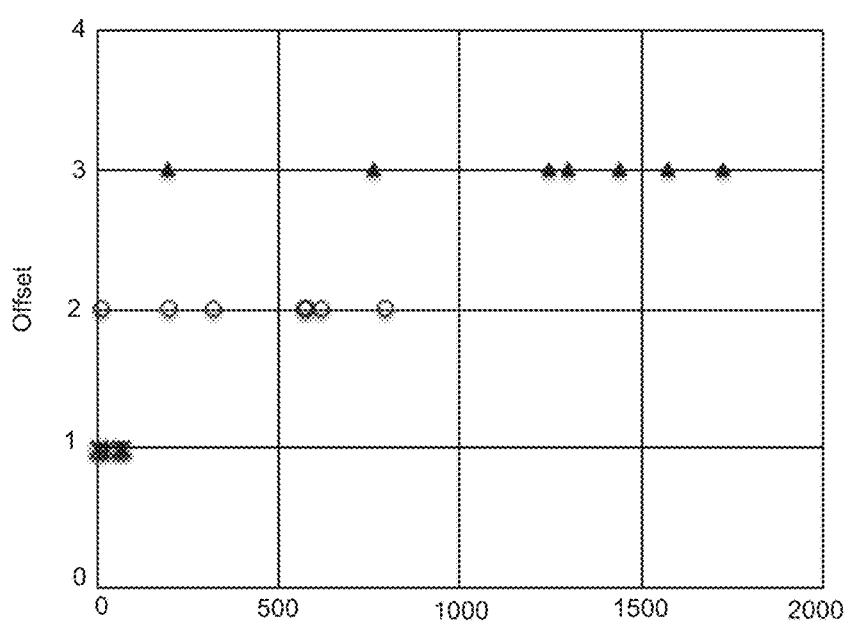
FIG. 9 is a graph illustrating the output of fluorometer Channel 3 (Ch3) in response to Kuwait oil samples with different DOR ratios pertaining to Example 1.

To verify if response of Ch3 alone can be used to differentiate oil dispersion states, all sample data points should be displayed along the 1D axis which corresponds to Ch3 (Channel 3) value. For easy visualization, the three groups of data, characterized by three oil dispersion states, were offset by one unit along the y axis as shown in FIG. 9. The mean value of Ch3 response increases from 33 mV for pure Kuwait oil samples to 444 mV for Kuwait oil/dispersant mixture (DOR=1/45), followed by oil dispersant mixture (DOR=1/20) which has the mean Ch3 response value of 1175 mV. The increase of the mean Ch3 output suggests improved dispersion. However, the three data sets, when projected to the Ch3 axis, show evident overlap with each other. In other words, the three groups of data are not considered statistically different and cannot be effectively discriminated according to their characterized state of dispersion. The overlap is mainly due to variable oil loading during the experiment, which commonly and inevitably occurs in the field environment due to variation in thickness of oil slicks.

Figure 10:
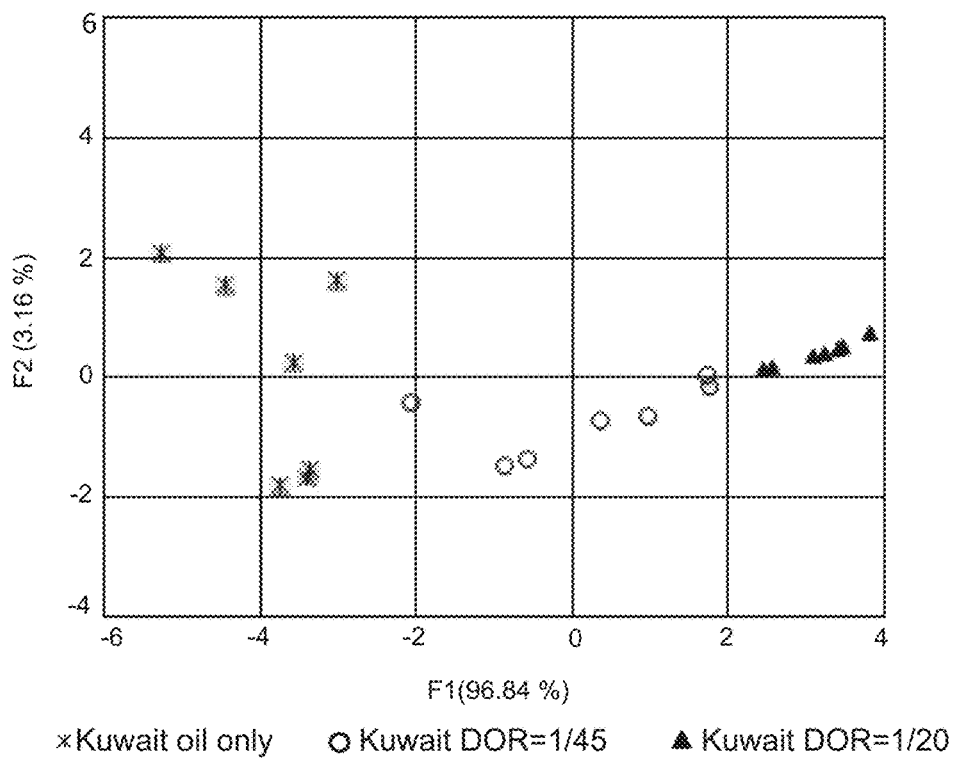
FIG. 10 is a graph illustrating discriminant analysis of fluorometer responses (Ch1, Ch2 and Ch3) to Kuwait oil samples with different DOR ratios pertaining to Example 1.

A method was developed to extract information on characteristic property changes of the dispersed oil. The method combines sensor outputs from all three fluorometer channels and extracts feature patterns to discriminate different states of dispersed oil. The sensor responses from three fluorometer channels were pre-treated with baseline correction followed by normalization (divided by the sum of sensor outputs from three fluorometer channels) and then processed with Linear Discriminate Analysis. In FIG. 10, sample data at three dispersion states were displayed in a plane formed by the first two principal components F1 and F2 from LDA, with F1 representing over 96% of sample variation. It can be observed that oil samples with increased DOR ratios showed an evident trend of red shift and all three states can be clearly discriminated with no detectable overlap.

Figure 11:
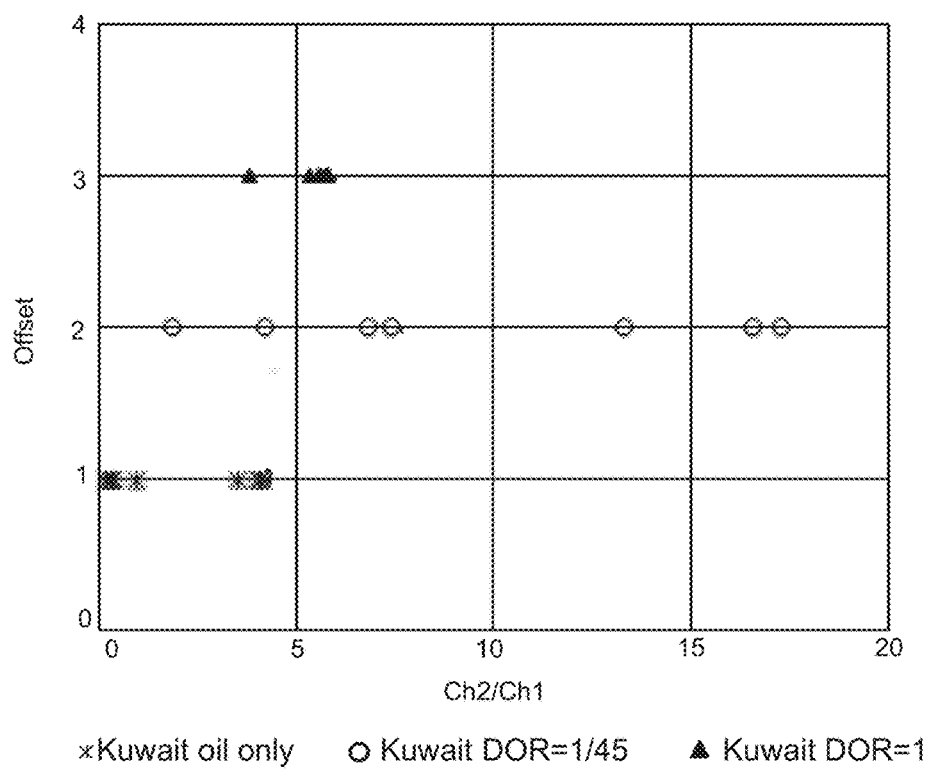
FIG. 11 is a graph illustrating ratios of fluorometer responses between Ch2 and Ch1 (Ch2/Ch1) (also known as the Fluorescence Intensity Ratio) to Kuwait oil samples with different DOR ratios pertaining to Example 1.

An alternative method, recorded in reference paper (Kepkay et al., 2008), is to use the ratio between two fluorometer channels to indicate effective oil dispersion. In this case, data were treated similarly as in FIG. 9, except the X axis corresponds to the ratio of Ch2/Ch1 instead of Ch3. As shown in FIG. 11, apparent overlaps still exist between the data sets and effective discrimination cannot be achieved.

To summarize, the proposed multi-variate analysis method in this patent demonstrates greatly improved ability to differentiate oils at different dispersion states. The information will provide distinct indication and straightforward interpretation of oil dispersion states, which will subsequently provide clear guidance for informed decision making.

Figure 12:
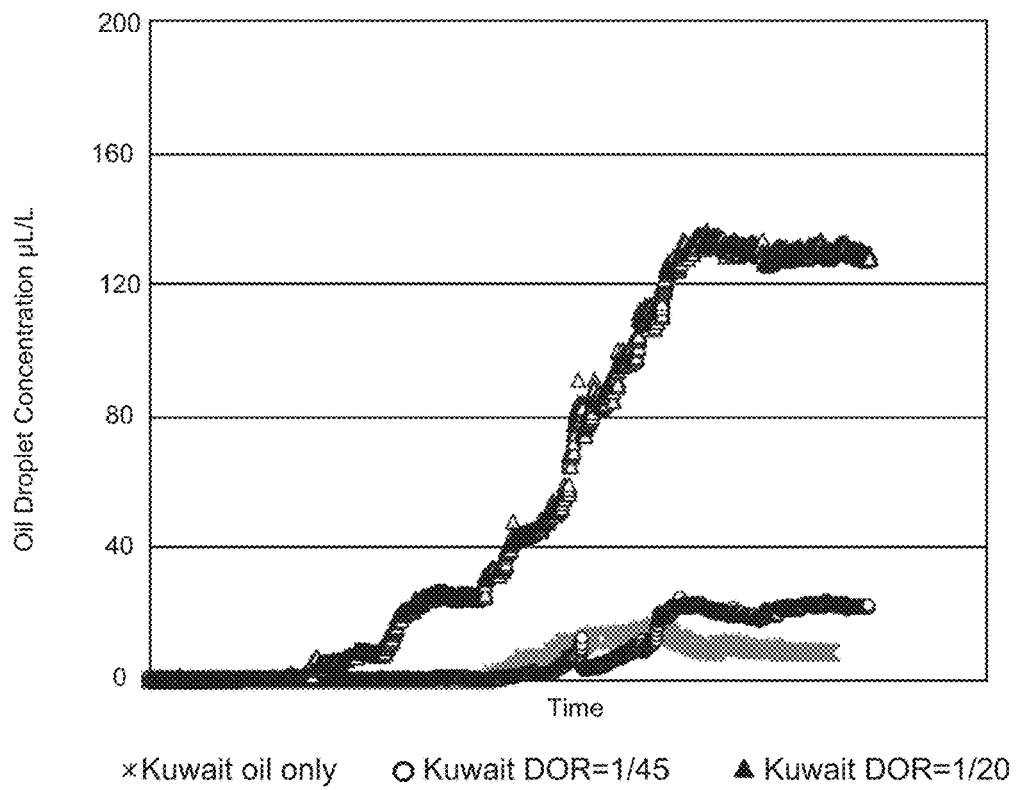
FIG. 12 is an output derived from the particle size analyzer illustrating the concentration of oil droplet of dispersed Kuwait oil samples with different DOR ratios pertaining to Example 1.

The concentration increase of dispersed oil droplets can also be confirmed by the concentration/time chart (FIG. 12) derived from the particle analyzer response. The oil droplet concentration shows the same trend as the fluorometer 20 with higher concentration value for oil samples mixed with more dispersant (DOR=1/20). However it is worth noting that when oil loading is low and the dispersed oil is below the particle analyzer's detection limit, the particle analyzer failed to detect any oil droplets despite their existence. This observation is consistent with our understanding of the detection limits of the particle analyzer 30.

Figure 13:
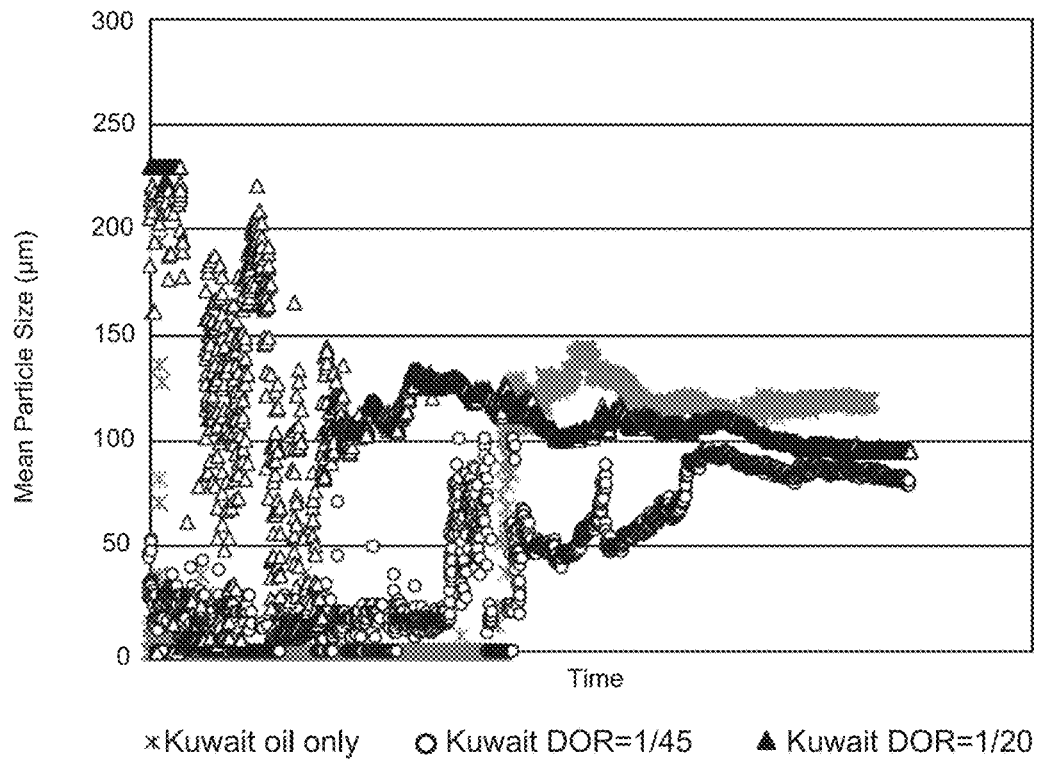
FIG. 13 is an output derived from the particle size analyzer illustrating the mean particle size of dispersed oil samples pertaining to Example 1.

FIG. 13 shows the mean particle size changes of dispersed oil with respect to time for different oil mixtures with different DORs. It reveals that the mean particle size dispersed from the pure oil is 125 nm. The mean particle side reduced dramatically to 85 nm for oil samples with 1/45 of DOR and then mildly increased to 95 nm for oil samples with 1/20 DOR. The observation agrees with the experiment conducted in 1981 (Martinelli, 1981) which shows that applying dispersant can significantly reduce the particle size of dispersed oil droplets in water, while increasing dispersant dosing rate may have mild influence on further change of the particle size and only increasing the amount of oil treated and subsequently the concentration increase of oil in water column. It is also worth noting that when oil loading is low and the dispersed oil in water is below the particle analyzer's detection limit, the derived mean particle size displays high level of noise (FIG. 13) which makes the data not valid for further analysis and interpretation.

The Kuwait oil at 1/20 DOR is better dispersed as characterized by the red shift of sample data from multi variant data analysis, as well as the enhanced oil concentration derived from both the fluorometer 20 and the particle analyzer 30. The mean particle size of the dispersed Kuwait oil at 1/20 DOR is 95 nm, much smaller compared to oil droplet dispersed from pure Kuwait oil, which has a mean oil droplet size of 125 nm, slightly bigger than the Kuwait oil at 1/45 DOR's mean particle size of 85 nm.

In the actual field deployment scenario, both sensor probes 20, 30 will be mounted to the deployment platform frame 100 that allows the sensors 20, 30 to continuously survey water along a pre-determined path. Data output from the two sensors 20, 30, together with time stamp and geographic coordinates, will be directly logged into the data base. Data will be processed and visualized the same way except that an ArcGIS (software) map overlayed with sensor response level will be provided to give an overview of sensor response with respective to the oil slick and its geographical location. Statistical analysis and pattern analysis of sensor data from multiple filed transects following dispersant application will be used to determine oil dispersion states and hence dispersant effectiveness.

Example 2: Prediction of Oil Dispersant Efficiency

With the objectives to validate sensors 20, 30 employed in oil dispersant efficacy monitoring system 200 in a large scale simulated field conditions and improve corresponding data analysis and visualization modules, a series of experiments were performed in a 30,000 L flume tank, operating in recirculation mode, at the BIO (Bedford Institute of Oceanography). The sensors 20, 30 were exposed to increasing dose of Heidrun oil premixed with four variable ratios (DOR=0, 1/100, 1/50 and 1/25) of Corexit 9500 dispersant and dispersed by the water flow in the flume tank. During each experiment, five injections of oil/dispersant mixture of 30 g, 30 g, 60 g, 120 g and 240 g were introduced to the flume tank in sequence. Water in the flume tank was allowed to equilibrate before sample collections followed by the next injection of oil/dispersant mixture. TPH (Total Petroleum Hydrocarbon) analysis of water samples, collected at nine locations evenly distributed inside the flume tank, was also conducted. Sensor outputs were continuously collected throughout the experiments.

Data Analysis

Dispersant Efficacy was calculated using the following formula:

=Oil in the water column/Total oil added into the tank100%

=Average TPH concentration in the tank (ppm)
\*Flume tank volume/Total oil injected into the tank100%.                Dispersant Efficacy (DE)

Average TPH concentration value was derived by averaging TPH analysis results of the samples collected at nine locations in the flume tank.

Multi-variate analysis was adopted to treat the sensor output from all three fluorometer channels. The ratio between the two Principal Components, PC2 and PC1, was used to create a model for DE prediction.

Results and Discussion

Due to the complexity of open water nature in the field and difficulty in quantifying the volume of oil slick, field monitoring and evaluation of chemical Dispersion Efficiency (DE) proves very difficult. In order to test the capability of the system 200 to predict/quantify Dispersant Efficacy in the field, a quantitative measurement of oil dispersion states, a method to use sensor responses from multiple sensors to predict DE was developed.

Principal Component Analysis (PCA) of the output from all 3 fluorometer channels showed that the first and the second Principal Components generated through the analysis could describe 99% of sample variance. The ratio between the two Principal Components PC2 and PC1 was used to create the model for DE prediction.

Figure 14:
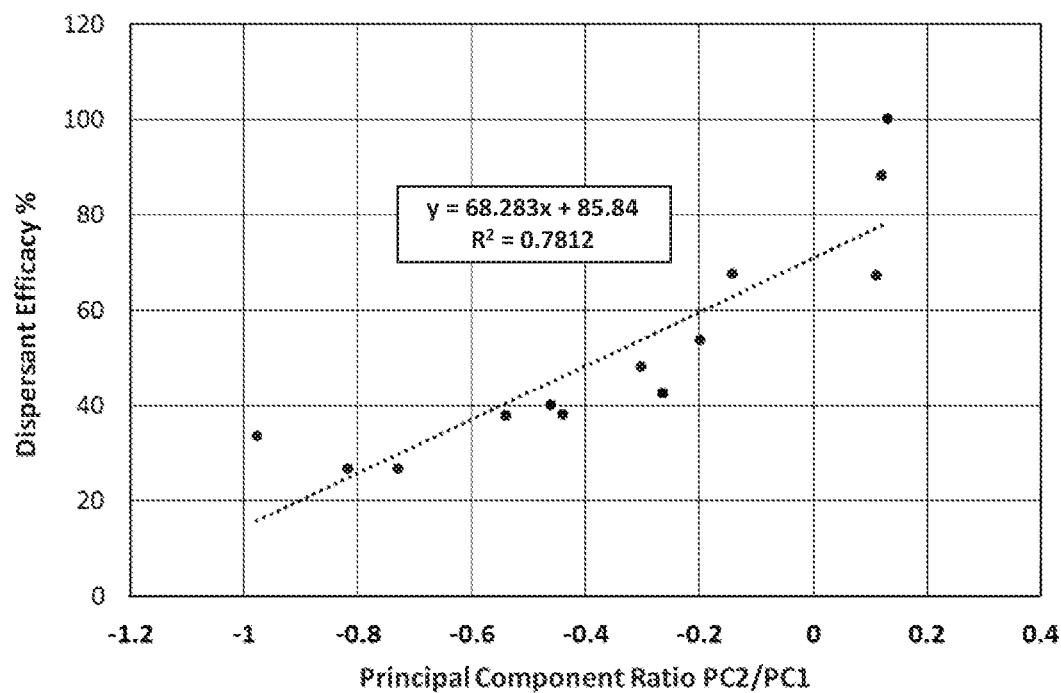
FIG. 14 is a graph illustrating normalized dispersant efficacy (DE) plotted against the ratio of two main principal components (PC2/PC1) with a linear trend line fit pertaining to Example 2.
Figure 15:
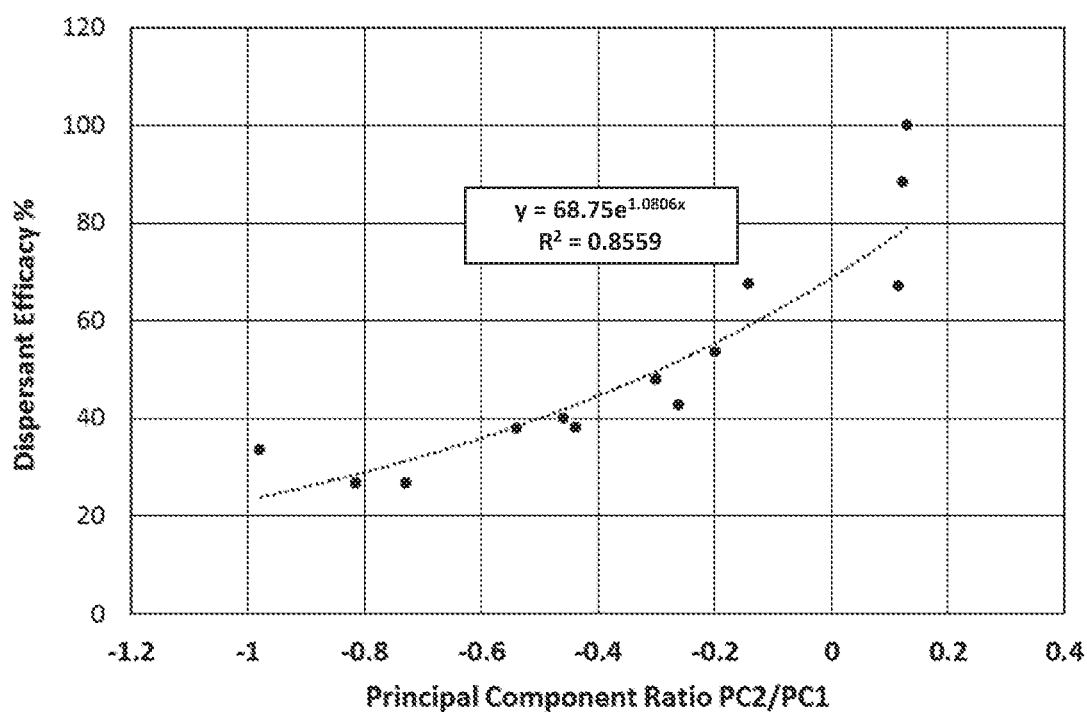
FIG. 15 is a graph illustrating normalized dispersant efficacy (DE) plotted against the ratio of two main principal components (PC2/PC1) with an exponential trend line fit pertaining to Example 2.

As shown in FIG. 14, DE was plotted against the ratio of the two main Principal Components. The two variables demonstrated good correlation with a $R^2$ value of 0.7812 when fitting with a linear trend line. An exponential trend line fit yielded even better correlation with a $R^2$ value of 0.8559 as shown in FIG. 15.

Figure 16:
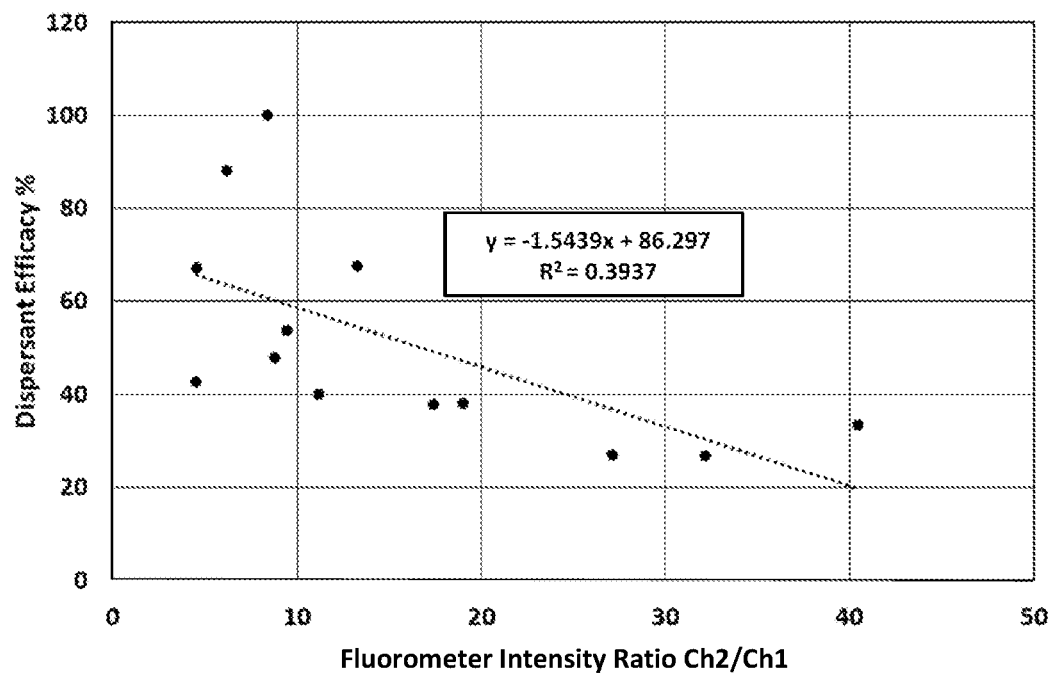
FIG. 16 is a graph illustrating normalized dispersant efficacy (DE) plotted against Fluorescence Intensity Ratio between fluorometer Channel 2 and Channel 1 (Ch2/Ch1) with a linear trend line fit pertaining to Example 2.

In comparison, when DE was plotted against Fluorescence Intensity Ratio between Ch2 and Ch1, as shown in FIG. 16, poor correlation was revealed between the two variables, especially in the range of medium to high DEs, with $R^2$ value of 0.3937. Therefore, Fluorescence Intensity Ratio is not suitable to be used to quantify Dispersant Efficacy in an open environment where untreated oil concentration can vary significantly.

Figure 17:
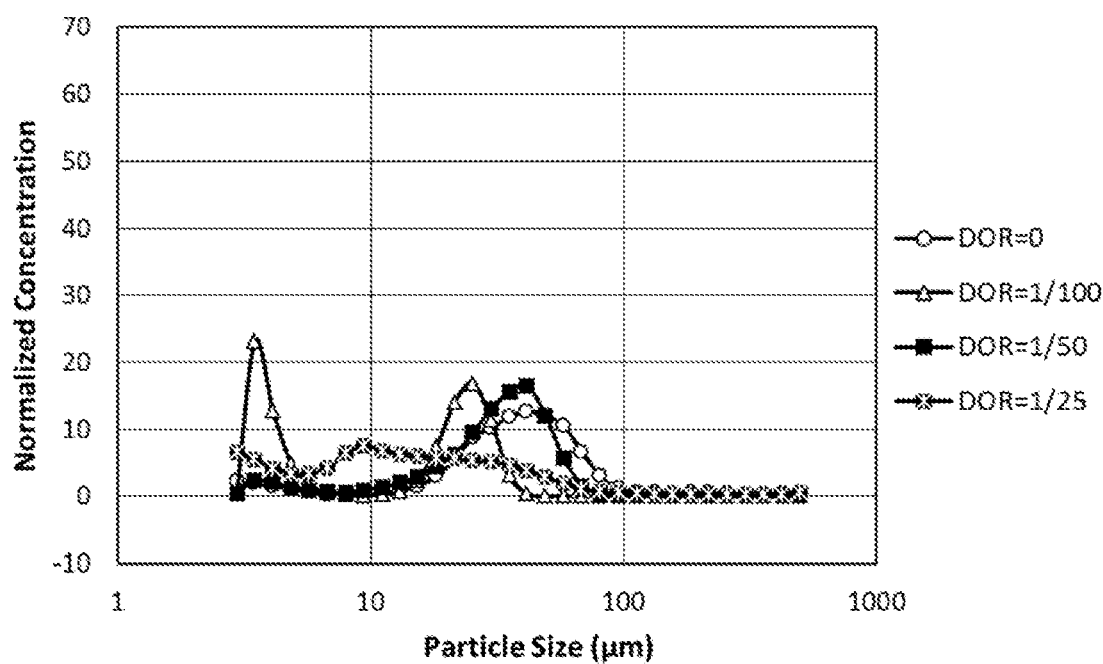
FIG. 17 is a particle size distribution histogram of dispersed oil samples using output derived from the particle sizer analyzer pertaining to Example 2.

Table 1 shows the mean particle size of oil droplets suspended in the flume tank during the four series of experiments and the corresponding DE measured and the DOR of oil samples used. The corresponding particle size distribution histogram is shown in FIG. 17. Table 1 indicates that DE consistently increased with increasing DOR, however the mean particle size measured by the particle size analyzer did not show consistent droplet size reduction. Accordingly, with increasing DOR, the mean particle size showed a sharp drop from 31.4 μm (DOR=0) to 8.0 μm (DOR=1/100) followed by a slight increase to 18.0 μm (DOR=1/50) and settled at 14.5 μm (DOR=1/25). Therefore, the mean particle size data from the particle analyzer is not recommended to be viewed individually as an indication of oil dispersion state. Instead, it should be used in conjunction with oil droplet concentration information as a confirmation of well chemically dispersed oil, which generally features significant reduction of oil droplet size and greatly increased oil droplet concentration compared to naturally dispersed oil.

TABLE 1

Mean particle size of oil droplets suspended in the flume tank and the corresponding DOR and DE

| Dispersant to oil ratio (DOR) | Dispersant Efficacy (DE) (%) | Mean particle size (μm) |
| --- | --- | --- |
| 0 | 26.8 | 31.4 |
| 1/100 | 39.9 | 8.0 |
| 1/50 | 47.8 | 18.0 |
| 1/25 | 67.1 | 14.5 |

In conclusion, the method developed established good correlation between ratios of the two main Principal Components generated from the multi-variate analysis of sensor responses and the DE derived from the average TPH concentration of oil suspended in water and the total oil loaded. The correlation model can be used to provide a quantitative estimate of DE based on sensor response data collected in the field. In comparison, the Fluorescence Intensity Ratio method as described in the prior art failed to generate a reasonable correlation that could justify its applicability in quantifying DE in an open field environment. Furthermore, mean particle size data from the particle analyzer can be used with oil droplet concentration information as a confirmation of well chemically dispersed oil.

It is to be understood that the following claims are provided by way of example only, and are not intended to limit the scope of what may be claimed in any future application. Features may be added to or omitted from the claims at a later date so as to further define or re-define the invention or inventions.

REFERENCES

Qi, X., Helmond, I., Crooke, E., Sherlock, M., Ross, A., Lee, K. and Irving, P., "Rapid dispersant efficacy monitoring equipment for oil spill response", In Proceedings of the 38th AMOP Technical Seminar, Vancouver, Canada, 722-734, 2015.

Lunel, T., "Dispersant effectiveness at sea", In Proceedings of the 1995 International Oil Spill Conference, Portland, Oreg. abs141, 2011.

Kepkay, P. E., C. W. Yeung, J. B. C. Bug den, Z. Li and K. Lee, "Ultraviolet fluorescence spectroscopy (UVFS): A new means of determining the effect of chemical dispersant on oil spills", in Proceedings of the 2008 International Oil Spill Conference, Savannah, Ga., 1: 639-643, 2008.

Martinelli, F. N., "The use of a laboratory wave tank to assess oil spill dispersants", 1981. USCG, NOAA, US EPA, CDC&P, MMS. "Special Monitoring of Applied Response Technologies" Version 8, 2006.

The invention claimed is:

1. A process for the determination of oil dispersant effectiveness, the process comprising:
   A. passing a submersible dispersant sensing platform across a body of water, said platform having a plurality of sensors including a multichannel fluorometer and a particle size analyzer, each sensor producing an output data stream;
   B. continuously analyzing the body of water at a predetermined depth profile below the surface of the body of water;
   C. collecting hydrodynamic and environmental condition data proximate in time and location to the output data from the dispersant sensing platform, said environmental condition data including one or more of: ambient temperature, body or water temperature, salinity of the body of water, wind speed, location, mixing energy of the body of water and derivatives thereof;
   D. providing oil and dispersant data including characteristics of the dispersant and of oil samples prior to the application of the dispersant; and
   E. processing the output data stream, the hydrodynamic and environmental condition data, and the oil and dispersant data to generate an indicator of the state of dispersion of the oil and of the oil dispersant efficiency under the hydrodynamic and environmental conditions to which the oil is exposed so as to determine the oil dispersant effectiveness.

2. The process according to claim 1, wherein E further includes analyzing the oil dispersant efficiency through multi-variate analysis.

3. The process according to claim 2, wherein the analysis involves linear discriminant analysis.

4. The process according to claim 2, wherein the analysis uses a database including one or more of:
   (i) characteristics of oil samples prior to the application of the dispersant;

(ii) sensor output when monitoring oil samples at various stages of dispersion within a field environment;
(iii) sensor output when monitoring oil samples at various stages of dispersion within a controlled environment;
(iv) hydrodynamic and environmental condition data in respect to (ii) and/or (iii);
(v) characteristics of the dispersant; and
(vi) correlations or models based upon (iii) and dispersion efficiency (DE) under one or more of (i), (iv) and (v).

5. The process according to claim 4, wherein the correlations or models are used to predict the oil dispersion characteristics over time, under a specific set of hydrodynamic and environmental conditions.

6. The process according to claim 4, wherein at least a portion of the database includes oil dispersant efficacy data and obtained sensor output when monitoring oil samples at various stages of dispersion within a controlled environment, wherein the controlled environment is a testing tank with controlled hydrodynamic and environmental conditions or an open field environment with controlled oil release.

7. The process according to claim 1, wherein E further includes analyzing the state of dispersion of the oil through pattern analysis.

8. The process according to claim 1, wherein E further includes quantitatively estimating or determining the oil dispersant efficiency.

9. The process according to claim 1, wherein the submersible dispersant sensing platform further includes a depth sensor to monitor the distance of the sensors from the surface of the body of water.

10. The process according to claim 1, wherein the submersible dispersant sensing platform further includes a temperature sensor to monitor water temperature.

11. The process according to claim 1, further comprising:
recording hydrodynamic and environmental condition data and the sensor output data (D0) during transit in control area with no oil slick for baseline correction;
recording hydrodynamic and environmental condition data and sensor output data (D1) during transit in area below oil slick prior to dispersant A application; and
recording hydrodynamic and environmental condition data and sensor output data (D2) during transit in area below oil slick post to dispersant A application,
wherein E is used to identify relative spatial difference between the naturally dispersed oil and chemically dispersed oil to decide if the two groups of sensor output data D1 and D2 are statistically different.

12. The process according to claim 1, further comprising:
recording hydrodynamic and environmental condition data and sensor output data (D0) during transit in control area with no oil slick for baseline correction;
recording hydrodynamic and environmental condition data and sensor output data (D1) during transit in area below oil slick prior to dispersant application;
recording hydrodynamic and environmental condition data and sensor output data (DA) during transit in area below oil slick post to dispersant A application;
recording hydrodynamic and environmental condition data and sensor output data (DB) during transit in area below oil slick post to dispersant B application; and
recording hydrodynamic and environmental condition data and sensor output data (DC) during transit in area below oil slick post to dispersant C application,
wherein E is used to determine if the corresponding groups of sensor output data DA, DB and DC are statistically different and, if so, quantify the spatial distance between groups.

13. The process according to claim 1, further comprising:
recording hydrodynamic and environmental condition data and sensor output data (D0) during transit in control area with no oil slick for baseline correction;
recording hydrodynamic and environmental condition data and sensor output data (D1) during transit in area below oil slick prior to dispersant A application;
recording hydrodynamic and environmental condition data and sensor output data (DOR1) during transit in area below oil slick post to dispersant A application at predetermined DOR (Dispersant vs Oil ratio);
recording hydrodynamic and environmental condition data and sensor output data (DOR2) during transit in area below oil slick post to dispersant A application with increased DOR; and
recording hydrodynamic and environmental condition data and sensor output data (DOR3) during transit in area below oil slick post to dispersant A application with further enhanced DOR,
wherein E is used to determine if the corresponding groups of sensor output data DOR1, DOR2 and DOR3 are statistically different.

14. A non-transitory computer readable medium, in which a computer program is stored which, when executed by a processor, is adapted to control or carry out the process according to claim 1.

15. A system for the determination of oil dispersant effectiveness, the system including:
a submersible dispersant sensing platform including a multichannel fluorometer and a particle size analyzer each producing an output data stream;
a means to pass the submersible dispersant sensing platform through a body of water;
a source of oil and dispersant data including characteristics of the dispersant and of oil samples prior to the application of the dispersant;
a source of hydrodynamic and environmental condition data;
a processing unit configured for receiving the output data stream, the hydrodynamic and environmental condition data, and the oil and dispersant data, and for generating an indicator of the state of dispersion of the oil and of the oil dispersant efficiency under the hydrodynamic and environmental conditions to which the oil is exposed so as to determine the oil dispersant effectiveness; and
a communication means for communicating the output data stream, the hydrodynamic and environmental condition data, and the oil and dispersant data to the processing unit.

16. The system according to claim 15, wherein the processing unit further includes a sub-module configured for pre-processing the output data stream and pre-processing the hydrodynamic and the environment condition data.

17. The system according to claim 16, wherein the pre-processing is used for any one or more of:
baseline corrections from a body of water including no oil slick and/or dispersant, and
monitoring and/or correcting for variations in sensor depth and/or water temperature.

18. The system according to claim 15, wherein the submersible dispersant sensing platform further includes a turbidity sensor producing an output data stream to correct for interference from a field water matrix effect.

19. The system according to claim 15, further including a database including one or more of:

(i) characteristics of oil samples prior to the application of the dispersant;
(ii) sensor output when monitoring oil samples at various stages of dispersion within a field environment;
(iii) sensor output when monitoring oil samples at various stages of dispersion within a controlled environment;
(iv) hydrodynamic and environmental condition data in respect to (ii) and/or (iii);
(v) characteristics of the dispersant; and
(vi) correlations or models based upon (iii) and dispersion efficiency (DE) under one or more of (i), (iv) and (v).

20. The system according to claim 19, wherein the sensor output (ii) includes at least sensor output from the multichannel fluorometer.

21. The system according to claim 15, wherein the multichannel fluorometer is configured to measure the emission fluorescence of an aqueous solution over the wavebands of at least a portion of each wavelength band 300 nm to 380 nm, 360 nm to 520 nm, and 410 nm to 600 nm using a corresponding excitation band length of at least a portion of each wavelength band between 214 nm and 294 nm, 214 nm and 294 nm, and 205 nm and 445 nm, respectively.

* * * * *